United States Patent
Kelley et al.

(10) Patent No.: US 12,364,764 B2
(45) Date of Patent: Jul. 22, 2025

(54) SUSTAINED RELEASE THERMOSETTING GELS COMPRISING SODIUM CHANNEL BLOCKERS AND THE METHODS OF MAKING SAME

(71) Applicant: Pacira Therapeutics, Inc., Burlington, MA (US)

(72) Inventors: Scott Kelley, Burlington, MA (US); Ujjwal Joshi, Burlington, MA (US); Ami Jo, Burlington, MA (US); John Derek Jackson, Burlington, MA (US); Rebecca Senter, Boston, MA (US); Neil Bodick, Boston, MA (US)

(73) Assignee: Pacira Therapeutics, Inc., Brisbane, CA (US)

( * ) Notice: Subject to any disclaimer, the term of this patent is extended or adjusted under 35 U.S.C. 154(b) by 806 days.

(21) Appl. No.: 17/640,090

(22) PCT Filed: Sep. 9, 2020

(86) PCT No.: PCT/US2020/049826
§ 371 (c)(1),
(2) Date: Mar. 3, 2022

(87) PCT Pub. No.: WO2021/050470
PCT Pub. Date: Mar. 18, 2021

(65) Prior Publication Data
US 2022/0296719 A1  Sep. 22, 2022

Related U.S. Application Data

(60) Provisional application No. 63/026,369, filed on May 18, 2020, provisional application No. 62/958,212, filed on Jan. 7, 2020, provisional application No. 62/932,076, filed on Nov. 7, 2019, provisional application No. 62/897,555, filed on Sep. 9, 2019.

(51) Int. Cl.
| | |
|---|---|
| *A61K 31/40* | (2006.01) |
| *A61K 9/00* | (2006.01) |
| *A61K 31/407* | (2006.01) |
| *A61K 47/34* | (2017.01) |
| *A61P 25/04* | (2006.01) |

(52) U.S. Cl.
CPC ............ *A61K 47/34* (2013.01); *A61K 9/0024* (2013.01); *A61K 31/407* (2013.01); *A61P 25/04* (2018.01)

(58) Field of Classification Search
CPC ......... A61K 31/407; A61P 29/00; A61P 25/04
USPC ......................................................... 514/409
See application file for complete search history.

(56) References Cited

U.S. PATENT DOCUMENTS

| | | |
|---|---|---|
| 8,450,358 B2 | 5/2013 | Chafeev et al. |
| 9,480,677 B2 | 11/2016 | Chafeev et al. |
| 10,118,932 B2 | 11/2018 | Ben-David et al. |
| 10,513,526 B2 | 12/2019 | Ben-David et al. |
| 2004/0241243 A1 | 12/2004 | Lin et al. |
| 2017/0095449 A1 | 4/2017 | Winters et al. |
| 2017/0239183 A1 | 8/2017 | Reynolds et al. |
| 2018/0311167 A1 | 11/2018 | Li |
| 2019/0071449 A1 | 3/2019 | Ben-David et al. |

FOREIGN PATENT DOCUMENTS

| | | |
|---|---|---|
| WO | WO 17/147147 | 8/2017 |
| WO | WO 21/050470 | 3/2021 |

OTHER PUBLICATIONS

Cox et al., Dec. 14, 2006, An SCN9A channelopathy causes congenital inability to experience pain, Nature, 444(7121):894-898.
Cummins et al., Sep. 22, 2004, Electrophysiological properties of mutant NAv1.7 sodium channels in a painful inherited neuropathy, The Journal of Neuroscience, 24(38):8232-8236.
Dib-Hajj et al., Jan. 2013, The Nav1.7 sodium channel: from molecule to man, Nature Reviews: Neuroscience, 15:49-62.
Fertleman et al., Dec. 7, 2006, SCN9A mutations in paroxysmal extreme pain disorder: allelic variants underlie distinct channel defects and phenotypes, Neuron, 52:767-774.
Yang et al., 2004, Mutations in SCN9A, encoding a sodium channel alpha subunit, in patients with primary erythermalgia, J Med Genet, 41:171-172.
International search report and written opinion dated Mar. 18, 2021 in application No. PCT/US20/49826.

*Primary Examiner* — Charanjit Aulakh
(74) *Attorney, Agent, or Firm* — Knobbe, Martens, Olson & Bear, LLP

(57) ABSTRACT

The present disclosure provides compositions comprising a thermosensitive hydrogel formulation of funapide and a tri-block polymer, and methods of use and manufacture of the compositions for management of acute pain or pain associated with surgical procedure.

24 Claims, 20 Drawing Sheets

SUSTAINED RELEASE THERMOSETTING GELS COMPRISING SODIUM CHANNEL BLOCKERS AND THE METHODS OF MAKING SAME

CROSS-REFERENCE TO RELATED APPLICATIONS

This application is a U.S. National Phase Application, filed under 35 U.S.C. § 371 (c), of International Application No. PCT/US2020/049826, filed Sep. 9, 2020, which claims the benefit of U.S. Provisional Application No. 63/026,369, filed on May 18, 2020; U.S. Provisional Application No. 62/958,212, filed on Jan. 7, 2020; U.S. Provisional Application No. 62/932,076, filed on Nov. 7, 2019; and U.S. Provisional Application No. 62/897,555, filed on Sep. 9, 2019, the contents of each of which are hereby incorporated by reference in their entirety.

FIELD OF THE INVENTION

The present disclosure describes compositions and methods directed to treating or managing pain where the compositions comprise funapide formulated in a tri-block copolymer. The present disclosure also provides methods of manufacturing the compositions, as described herein.

BACKGROUND OF THE INVENTION

There are an estimated 70 million surgical procedures completed in the United States each year (Owings 1998). Over 80% of patients who undergo surgical procedures experience acute postsurgical pain and ~75% of those patients report their pain severity as moderate, severe or extreme (Chou 2016). In more than 50% of cases, patients report not receiving adequate pain relief following their procedure (Chou 2016). Inadequately controlled postsurgical pain can have both short- and long-term effects, including negative effects on quality of life, function and functional recovery, the risk of postsurgical complications, and the risk of persistent postsurgical pain.

There is a substantial unmet need in postsurgical pain management for a non-opioid sensory blockade with an extended regional analgesia effect that does not materially compromise motor function. Orthopedic surgery generates the second-highest rates of opioid prescriptions among adults, with many patients using opioids both before and after surgery (Smith 2018), facilitating a path to potential addiction. A treatment that provides extended pain relief while not materially impairing motor function could reduce the need for opioids, allow for earlier ambulation and physical therapy, and provide the ability for patients to leave the hospital sooner after surgery.

Funapide is a small molecule voltage-gated sodium channel (Nav) inhibitor that preferentially antagonizes Nav1.7. Nav1.7 is involved in pain signaling based on human phenotypes resulting from mutations in the SCN9A gene, where loss of function results in congenital insensitivity to pain (CIP) and gain of function results in hypersensitivity to pain (Yang 2004, Fertleman 2006, Goldberg 2007). Antagonism of Nav1.7 is sufficient to provide analgesia from postsurgical pain without materially impairing motor function. There is an unmet need for a pharmaceutical composition to deliver durable pain relief with a single injection. Disclosed herein is a thermosensitive hydrogel formulation comprising funapide that maintains local physical proximity and high local drug concentrations for at least 3-5 days at the site of targeted injection—a peripheral nerve—and can provide at least 3-5 days of postsurgical pain relief without materially impairing motor function.

SUMMARY OF THE INVENTION

The present disclosure provides a composition of funapide formulated in a PLGA-PEG-PLGA triblock copolymer, wherein the composition comprises: a) funapide at a concentration of 0.2 to 2% w/w; b) a PLGA-PEG-PLGA tri-block copolymer at a concentration of 5% to 35% w/w; (i) wherein each Poly-Lactic-co-Glycolic acid (PLGA) polymer block has a molecular weight (MW) of 400 to 2550 Da and wherein the Polyethylene Glycol (PEG) polymer block has a MW of 1000-3000 Da; and (ii) wherein the PLGA comprises 40% to 100% of lactic acid and 60% to 0% of glycolic acid; c) a polar organic solvent at a concentration of 1%-20% w/w; and d) a solubility enhancer at a concentration of 1% to 20% w/w.

The present disclosure provides a composition of funapide formulated in a PLGA-PEG-PLGA triblock copolymer, wherein the molecular weight values of the PLGA polymer and PEG polymer are reported on a number average (Mn) basis using a Gel Permeation Chromatography (GPC) method.

The composition can comprise a PLGA-PEG-PLGA triblock copolymer with each PLGA polymer block of MW 1000-2450 Da. The composition can comprise a PLGA-PEG-PLGA tri-block copolymer with each PLGA polymer block of MW 1400-2450 Da.

The composition can comprise a PLGA-PEG-PLGA tri-block copolymer with the PEG polymer block of MW 1000-1600 Da. The composition can comprise a PLGA-PEG-PLGA tri-block copolymer with the PEG polymer block of MW 1400-1600 Da.

The composition can comprise funapide at a concentration of 0.2% to 1.8% w/w. The composition can comprise funapide at a concentration of 0.2% to 1.5% w/w. The composition can comprise funapide at a concentration of 0.2% to 1% w/w. The composition can comprise funapide at a concentration of 1% to 2% w/w. The composition can comprise funapide at a concentration of 1% to 1.5% w/w. The composition can comprise funapide at a concentration of 1.5% to 2% w/w. The composition can comprise funapide at a concentration of 0.65% w/w. The composition can comprise funapide at a concentration of 1.3% w/w.

The composition can comprise a polar organic solvent at a concentration of 1% to 5% w/w. The composition can comprise a polar organic solvent at a concentration of 5% to 10% w/w. The composition can comprise a polar organic solvent at a concentration of 10% to 20% w/w. The composition can comprise a polar organic solvent at a concentration of 1.5%-20% w/w. The composition can comprise a polar organic solvent at a concentration of 1% to 10.5% w/w. The composition can comprise a polar organic solvent at a concentration of 1.5% to 2% w/w. The composition can comprise a polar organic solvent at a concentration of 1.5% w/w. The composition can comprise a polar organic solvent at a concentration of 1.7% w/w. The polar organic solvent can be any one of Dimethyl acetamide (DMA), Dimethyl sulfoxide (DMSO), Glycofurol, and N-Methyl-2-Pyrrolidone (NMP), or any combination thereof. The polar organic solvent can be DMA.

The composition can comprise a solubility enhancer at a concentration of 5%-20% w/w. The composition can comprise a solubility enhancer at a concentration of 10%/6-11% w/w. The solubility enhancer can be any one of propylene glycol (PG), Cremophor EL, Cremophor RH 60, Ethanol, Glycerin, PEG 300, PEG 400, polysorbates, Vitamin E-TPGS, PLGA-PEG diblock copolymers, hydroxypropyl-β-cyclodextrin, sulfobutyl ether-β-cyclodextrin, poloxamer 188, poloxomer 407, polyvinyl pyrrolidone (PVP), glycerol formal, and Solutol HS, or any combination thereof. Preferred solubility enhancers include polysorbates, PLGA-PEG diblock copolymers, Cremophor EL, PEG 300, PEG 400, and Solutol HS. In one preferred aspect the solubility enhancer can be PEG 400.

The composition can comprise a PLGA with 40% of lactic acid and 60% of glycolic acid (LA:GA ratio of 40:60). The composition can comprise a PLGA with 50% of lactic acid and 50% of glycolic acid (LA:GA ratio of 50:50). The composition can comprise a PLGA with 100% of lactic acid and 0% of glycolic acid (LA:GA ratio of 100:0).

The composition can comprise a PLGA-PEG-PLGA tri-block copolymer at a concentration of 8% to 25% w/w. The composition can comprise a PLGA-PEG-PLGA tri-block copolymer at a concentration of 19% to 20% w/w.

The total molecular weight of the total tri-block polymer system of the composition as disclosed herein can be between 2500-7000 Da. The total molecular weight of the total tri-block polymer system can be between 4000-7000 Da. The total molecular weight of the total tri-block polymer system can be between 6000-7000 Da. The total molecular weight of the total tri-block polymer system does not exceed more than 6600-7000 Da. The total molecular weight of the total tri-block polymer system can be 6000 Da.

The composition, as disclosed herein, can comprise a PLGA-PEG-PLGA tri-block copolymer that can be 400 Da-3000 Da-400 Da of PLGA-PEG-PLGA. The composition can comprise a PLGA-PEG-PLGA tri-block copolymer that can be 1000 Da-1000 Da-1000 Da of PLGA-PEG-PLGA. The composition can comprise a PLGA-PEG-PLGA tri-block copolymer that can be 1500 Da-1500 Da-1500 Da of PLGA-PEG-PLGA. The composition can comprise a PLGA-PEG-PLGA tri-block copolymer that can be 2000 Da-2000 Da-2000 Da of PLGA-PEG-PLGA. The composition can comprise a PLGA-PEG-PLGA tri-block copolymer that can be 2450 Da-1500 Da-2450 Da of PLGA-PEG-PLGA.

The composition can comprise: a) funapide at a concentration of 1.3% w/w; b) a PLGA-PEG-PLGA tri-block copolymer at a concentration of 19% to 19.5% w/w; (i) wherein each PLGA polymer blocks has a MW of 1500-2250 Da, and wherein the PEG polymer block has a MW of 1500 Da; and (ii) wherein the PLGA lactic acid:glycolic acid ratio (LA:GA ratio) is 50:50; c) DMA at a concentration of 1.7% w/w; and d) PEG 400 at a concentration of 10.5% w/w.

The composition can comprise: a) funapide at a concentration of 0.65% w/w; b) a PLGA-PEG-PLGA tri-block copolymer at a concentration of 19% to 19.5% w/w; (i) wherein each PLGA polymer block has a MW of 1500-2250 Da, and wherein the PEG polymer block has a MW of 1500 Da; and (ii) wherein the PLGA lactic acid:glycolic acid ratio (LA:GA ratio) is 50:50; c) DMA at a concentration of 1.7% w/w; and d) PEG 400 at a concentration of 10.5% w/w.

The composition can have a total dose volume of 5 ml to 40 ml. The composition can have a total dose volume of 5 ml. The composition can have a total dose volume of 10 ml. The composition can have a total dose volume of 15 ml. The total dose volume of the composition can be 20 ml. The composition can have a total dose volume of 25 ml. The composition can have a total dose volume of 30 ml. The composition can have a total dose volume of 40 ml.

The present disclosure provides a method of treatment for post-surgical pain in a subject in need thereof, wherein the method comprises administering to the subject an effective amount of any of the compositions disclosed herein. The method comprises administering to the subject an effective amount of any of the compositions to the subject prior to a surgical procedure. The method of treatment for post-surgical pain can comprise administering an effective amount of the composition to the subject during a surgical procedure. The method of treatment for post-surgical pain can comprise administering an effective amount of the composition to the subject following a surgical procedure. The method of treatment for post-surgical pain can comprise administering an effective amount of the composition to the subject prior to a surgical procedure.

The present disclosure provides a method of prevention or treatment for pain in a subject in need thereof, wherein the method comprises administering an effective amount of the compositions disclosed herein. The pain can be acute pain. The acute pain can be due to any one of an injury, dental work, labor and childbirth, a surgical procedure or any combination thereof.

The effective amount induces an analgesic nerve block. The analgesic nerve block can be any one of upper extremity nerve block, lower extremity nerve block, facial nerve block, neck and back nerve block, chest and abdominal blocks, or any combination thereof. The upper extremity nerve block can be any one or more of interscalene, supraclavicular, brachial plexus, infraclavicular, or any combination thereof. The lower extremity nerve block can be any one or more of hypogastric plexus, lumbar plexus, femoral nerve, adductor canal nerves, saphenous nerve, popliteal fossa and sciatic nerve, or any combination thereof. The facial nerve block can be any one or more of trigeminal, ophthalmic, supraorbital, maxillary, sphenopalatine, or any combination thereof. The neck and back nerve block can be any one or more of cervical epidural, thoracic epidural, lumbar epidural, caudal block or any combination thereof. The chest and abdominal block can be any one or more of paravertebral, intercostal, transversus abdominis plane, rectus sheath or any combination thereof.

The surgical procedure can be any one of diagnostic surgical procedure, ablative surgical procedure, palliative surgical procedure, reconstructive surgical procedure, transplantation surgical procedure, constructive surgical procedure, or any combination thereof.

The surgical procedure can be any one of upper extremity surgical procedure, lower extremity surgical procedure, abdominal surgical procedure, cardio-thoracic surgical procedure, head and neck surgical procedure, back surgical procedure, musculoskeletal surgical procedure, orthopedic surgical procedure, ocular surgical procedure, ear, nose and throat surgical procedure, vascular surgical procedure, dental surgical procedure, or any combination thereof.

The upper extremity surgical procedure can be any one of a surgical procedure of arm, forearm, hand, wrist, elbow, shoulder, or any combination thereof. The upper extremity surgical procedure can be a surgical procedure of one or more bone(s) of the arm, forearm, hand, wrist, elbow, shoulder, or any combination thereof. The one or more bone(s) can comprise any one of radius, ulna, humerus, carpals, metacrapals or phalanges or a combination thereof.

The lower extremity surgical procedure is any one of a surgical procedure of hip, thigh, knee, ankle, feet, or any combination thereof. The lower extremity surgical procedure can be a surgical procedure of one or more bone(s) of the hip, thigh, knee, ankle, feet, or any combination thereof.

The one or more bone(s) can comprise any one of acetabulum, femur, tibia, fibula, patella, tarsal bone, metatarsal bone, arches of the foot or a combination thereof.

The surgical procedure can be of any one of an abdominal wall, a thoracic wall or a combination thereof. The surgical procedure can be a surgical procedure of an organ. The organ can be heart, lung, liver, spleen, brain, stomach, small intestine, large intestine, gall bladder, bile ducts, lymphatic ducts, urinary bladder, prostate gland, pancreas, adrenal gland, thyroid gland, skin, uterus, fallopian tubes, ovary, seminal tubules, testes, or any combination thereof. The surgical procedure can be for any one of repair, removal or transplantation of the organ. The organ surgical procedure can be for removal of tumor or cancerous tissue from within or near the organ.

The subject in need thereof, can be a mammal. The subject can be a human, a murine, an equine, a canine, a feline, a rabbit, a pig, a hamster, a bovine or a camelid. The subject can be a human.

The effective amount of the composition is administered perineurally, epidurally, subcutaneously, intradermally, orally, intramuscularly or intravenously. The effective amount of the composition is preferentially administered perineurally. The effective amount of the composition is administered by direct instillation into a wound at the site(s) of an injury or a surgical procedure. The effective amount of the formulation is administered by infiltration at the site(s) of an injury or a surgical procedure.

The present disclosure provides a method of manufacturing any of the compositions disclosed herein, the method comprising: i) combining and dissolving: a) an amount of the PLGA-PEG-PLGA tri-block polymer; b) an amount of water; c) an amount of the funapide; d) an amount of the polar organic solvent; and e) an amount of the solubility enhancer; to form a mixture; ii) stirring the mixture of (i) at 1-30° C.; iii) filtering the clear solution of (ii) through a sterile filter; and iv) collecting and freezing the filtered solution of (iii) at ≤−20° C.

The method of manufacturing any of the compositions disclosed herein, can comprise in step i): 1) compounding and dissolving the amount of the PLGA-PEG-PLGA tri-block polymer of (a) in the amount of water of (b) at 1-30° C., to form a polymer solution; 2) dissolving the amount of the funapide of (c) in the amount of the polar organic solvent of (d) and the amount of the solubility enhancer of (e), in a separate vessel to form a funapide solution; and 3) combining the dissolved funapide solution of (2) with the polymer solution of (1) to form a mixture. In the method of manufacturing any of the compositions disclosed herein, temperature of stirring the mixture can be 1-30° C. Preferred temperature ranges include 5-25° C., 5-20° C. and 5-15° C. In one preferred aspect, the temperature ranges from 8-12° C.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claims.

BRIEF DESCRIPTION OF DRAWINGS

FIG. 1A depicts an in vitro release profile of a funapide-triblock polymer formulation (FX301) of the present disclosure. Percentage cumulative drug released (y-axis) is measured as a function of time (hours) (x-axis). Results are from one experiment comprising analysis of one formulation analyzed for IVR in triplicate. Statistical significance is indicated with SD error bars. FIG. 1B depicts the plasma PK profile of funapide achieved after sciatic nerve block application of FX301 in the post-surgical pig model. Plasma concentration of funapide (nM) (y-axis) is measured as a function of time (hours) (x-axis). Dashed line indicates in vitro $IC_{50}$ value of funapide inhibition of Nav1.7. Results are representative of 3 animals. Statistical significance is indicated with standard error of mean (SEM) error bars.

FIG. 2 depicts an in vitro release profile of six different formulations as indicated in Table 2, measured as % API released (y-axis) as a function of time (hours) (x-axis). Results are representative of a single experiment with in vitro release analysis using a single replicate, for each formulation as indicated.

FIG. 3 depicts the plasma pharmacokinetics of funapide in rats treated with six different formulations, as indicated in Table 2. Plasma concentration of funapide (nM) (y-axis) is measured as function of time (hours) (x-axis). Results are representative of 3 animals per group. Statistical significance is indicated with SEM error bars.

FIG. 4 depicts an in vitro release profiles of different formulations containing higher polymer concentrations, for each formulation as indicated in Table 3, measured as % API released (y-axis) as a function of time (hours) (x-axis). Results are representative of a single experiment for each formulation analysed.

FIG. 5 depicts plasma pharmacokinetics of funapide in rats treated with the different formulations, as indicated in Table 3. Plasma concentration of funapide (nM) (y-axis) is measured as function of time (hours) (x-axis). Results are representative of 3 animals. Statistical significance is indicated with SEM error bars.

FIG. 6 depicts in vitro release profiles of different formulations with or without polysorbate 80, as indicated in Table 4, measured as % API released (y-axis) as a function of time (hours) (x-axis). Results are representative of a single experiment for each formulation analysed.

FIG. 7 depicts an in vitro release profile of different polymer formulations with or without polysorbate 80, as indicated in Table 4, measured as total mass of API released (µg) (y-axis) as a function of time (hours) (x-axis). Results are representative of a single experiment for each formulation analysed.

FIG. 8 depicts the plasma pharmacokinetic profile from a PK study conducted in pig for in vivo exposure to formulation without polysorbate 80 using a 5 mL dosing volume, which was administered by perineural injection. Dashed line indicates in vitro $IC_{50}$ value of funapide inhibition of Nav1.7 (50 nM).

FIG. 9 depicts in vitro release profiles of different formulations with or without DMA, as indicated in Table 6, measured as % API released (y-axis) as a function of time (hours) (x-axis). Results are representative of a single experiment for each formulation analysed.

FIG. 10 depicts the plasma pharmacokinetics of funapide in rats treated with a dosage of 300 µl of the different formulations, as indicated in Table 6. Plasma concentration of funapide (nM) (y-axis) is measured as function of time (hours) (x-axis). In vitro $IC_{50}$ value indicated with dashed line. Results are representative of 3 animals per group. Statistical significance is indicated with SEM error bars.

FIG. 11 depicts the plasma pharmacokinetic profile of funapide in pigs treated with a dosage of 10 ml of an FX301 formulation. Plasma concentration of funapide (nM) (y-axis) is measured as function of time (hours) (x-axis). Dashed line indicates in vitro $IC_{50}$ value of funapide inhibition of Nav1.7. Results are representative of 3 animals. Statistical significance is indicated with SEM error bars.

FIG. 12 depicts the in vitro release profiles of a 19.2% low molecular weight (Low MW) (3600 Da) polymer formulation and a 19.2% high molecular weight (High MW) (5400 Da) polymer formulation, as indicated in Table 7, measured as % API released (y-axis) as a function of time (hours) (x-axis). Results are representative of single experiments for the high MW group and single experiment for the low MW group.

FIG. 13 depicts the plasma pharmacokinetics of funapide in rats treated with either a 19.2% low molecular weight (Low MW) (3600 Da) polymer formulation or a 19.2% high molecular weight (High MW) (5400 Da) polymer formulation, as indicated in Table 7. Plasma concentration of funapide (nM) (y-axis) is measured as function of time (hours) (x-axis). Dashed line indicates in vitro $IC_{50}$ value of funapide inhibition of Nav1.7. Results are representative of 3 animals per group. Statistical significance is indicated with SEM error bars.

FIG. 14 depicts an in vitro drug release profile of FX301 made with PLGA-PEG-PLGA polymer with MW in the range of 5600 to 6400 Da, in which the PEG polymer block MW is about 1500 Da, and the variation in total MW resulting from variation in the PLGA block MW (all polymers with 50% of lactic acid and 50% of glycolic acid (LA:GA 50:50)), as indicated in Table 8, measured as % API released (y-axis) as a function of time (hours) (x-axis). Results are representative of a single experiment with in vitro release analysis done in triplicate, for each formulation as indicated. Statistical significance is indicated with SD error bars.

FIG. 15A depicts Mean f SEM Withdrawal Force by von Frey testing. FIG. 15B depicts Mean f SEM GBS Score. FIG. 15C depicts Mean t SEM Total Walking Distance over 5 Minutes in Open-Field Testing. Bars represent each treatment group as indicated and error bars indicate SEM. Comparisons between treatment and vehicle groups were performed using one-way analysis of variance followed by Tukey test; *p<0.05 vs vehicle; p<0.01 vs vehicle; bupivacaine; ##p<0.01 vs liposomal bupivacaine; ####p<0.001 vs liposomal bupivacaine (one-way ANOVA followed by Tukey test). +p<0.05 vs baseline (repeated-measures ANOVA). *p<0.005; ****p<0.001 vs vehicle; #p<0.05 vs liposomal.

FIG. 16 depicts Funapide quantified in plasma of pigs treated with FX301, using high-performance liquid chromatography with tandem mass spectrometry detection. Plasma funapide concentration (ng/ml) (y-axis) was measured as a function of time (hours) (x-axis). Data is representative of n=3 animals, and error bars indicate SEM.

FIG. 17A depicts systemic funapide concentration profile measured as plasma concentration (ng/ml) (y-axis) as a function of time (hours) (x-axis). FIG. 17B depicts local muscle funapide concentrations measured as total concentration (ng/g) (y-axis) as a function of time (days) (x-axis).

DETAILED DESCRIPTION OF THE INVENTION

Figure 1B:
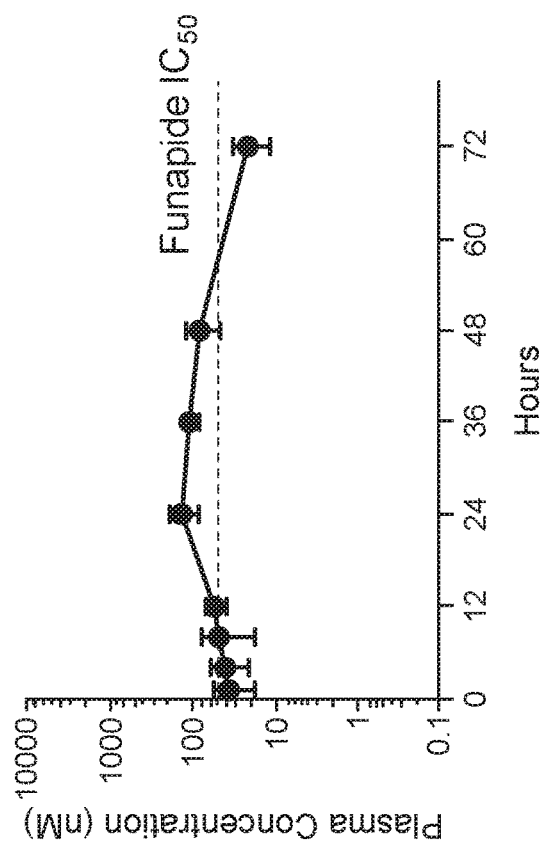
FIG. 1A-1B. In vitro and in vivo release of funapide-triblock polymer formulation.

Nav1.7 is a voltage-gated sodium channel that plays a critical role in the generation and conduction of action potentials along sensory neurons (Dib-Flajj S D, et al. Nat Rev Neurosci. 2013; 14: 49-62). Genetic evidence from inherited pain syndromes has provided validation of Nav1.7 as a therapeutic target for the treatment of pain (Cox J J, et al. Nature. 2006, 444:894-98; Fertleman C R, et al. Neuron. 2006; 52:767-74; Yang Y, et al. J Med Genet. 2004; 41:171-74; Cummins T R, et al. J Neurosci. 2004; 24:8232-36). As Nav1.7 is preferentially expressed by sensory neurons rather than motor neurons (Dib-Hajj S D, et al. Nat Rev Neurosci. 2013; 14:49-62), targeting Nav1.7 has the potential to provide effective pain relief while not materially impairing motor function. Thus there is a need in the art for compositions and methods targeting Nav1.7 for pain management. The present disclosure addresses these needs.

A thermosensitive hydrogel technology is disclosed herein for the delivery of a preferential Nav1.7 antagonist (funapide) for postsurgical pain management. The hydrogel is primarily composed of PLGA-PEG-PLGA tri-block copolymer. The triblock polymer upon dissolution in water self-assembles into nano-sized micelles. At ambient temperature, the formulation exists in a solution phase comprised of polymeric micelles which can be loaded with drug. Upon warming to body temperature, interactions between the hydrophobic domains of the micelles become thermodynamically favored, and the micelles form a network resulting in a phase transition from micellar solution into a viscous gel with a consistency similar to that of petroleum jelly. This process is fully reversible upon cooling. This solution to gel phase transformation allows for ease of injection as a solution, with quick conversion to a viscous gel phase once administered allowing for physical depot residency and controlled drug release by simple drug diffusion. A hydrophobic drug can be encapsulated within the hydrophobic core of micelles while the formulation is still liquid (below critical gelation temperature). Encapsulated drug then releases over several days from the gel depot of the formulation.

The structure of funapide is well known in the art, for example in U.S. Pat. Nos. 8,450,358, 9,480,677, 10,118,932 and 10,513,526, incorporated herein by reference.

The present disclosure provides a composition of funapide formulated in a PLGA-PEG-PLGA triblock copolymer, wherein the composition comprises: a) funapide; b) a PLGA-PEG-PLGA tri-block copolymer; c) a polar organic solvent; and d) a solubility enhancer. In the compositions of the present disclosure, the balance of compositional mass comprises water.

The present disclosure provides a composition of funapide formulated in a PLGA-PEG-PLGA triblock copolymer, wherein the composition comprises: a) funapide at a concentration of about 0.1 to 5% w/w; b) a PLGA-PEG-PLGA tri-block copolymer at a concentration of 5% to 35% w/w; (i) wherein each PLGA polymer block has a MW of about 300 to 3000 Da and wherein the PEG polymer block has a MW of about 700-3500 Da; and (ii) wherein the PLGA comprises 40% to 100% of lactic acid and 60% to 0% of glycolic acid; c) a polar organic solvent at a concentration of about 1%-20% w/w; and d) a solubility enhancer at a concentration of 1% to 20% w/w.

The present disclosure provides a composition of funapide formulated in a PLGA-PEG-PLGA triblock copolymer, wherein the composition comprises: a) funapide at a concentration of 0.2 to 2% w/w; b) a PLGA-PEG-PLGA tri-block copolymer at a concentration of 5% to 35% w/w; (i) wherein each PLGA polymer block has a MW of 400 to 2550 Da and wherein the PEG polymer block has a MW of 1000-3000 Da; and (ii) wherein the PLGA comprises 40% to 100% of lactic acid and 60% to 0% of glycolic acid; c) a polar organic solvent at a concentration of 1%-20% w/w; and d) a solubility enhancer at a concentration of 1% to 20% w/w.

The composition can comprise funapide at a concentration of 0.1 to 2% w/w. The composition can comprise funapide at a concentration of 0.2 to 2% w/w. The composition can comprise funapide at a concentration of 0.2 to 1.8% w/w. The composition can comprise funapide at a concentration of 0.2 to 1.5% w/w. The composition can comprise funapide at a concentration of 0.65 to 1.3% w/w. The composition can comprise funapide at a concentration of 0.5 to 1.0% w/w. The composition can comprise funapide at a concentration of 0.65% w/w. The composition can comprise funapide at a concentration of 1.3% w/w.

The composition can comprise a PLGA-PEG-PLGA tri-block copolymer at a concentration of 5-30% w/w. The composition can comprise a PLGA-PEG-PLGA tri-block copolymer at a concentration of 5-25% w/w. The composition can comprise a PLGA-PEG-PLGA tri-block copolymer at a concentration of 5-20% w/w. The composition can comprise a PLGA-PEG-PLGA tri-block copolymer at a concentration of 5-15% w/w. The composition can comprise a PLGA-PEG-PLGA tri-block copolymer at a concentration of 5-10% w/w. The composition can comprise a PLGA-PEG-PLGA tri-block copolymer at a concentration of 8-35% w/w. The composition can comprise a PLGA-PEG-PLGA tri-block copolymer at a concentration of 8-30% w/w. The composition can comprise a PLGA-PEG-PLGA tri-block copolymer at a concentration of 8-25% w/w. The composition can comprise a PLGA-PEG-PLGA tri-block copolymer at a concentration of 8-20% w/w. The composition can comprise a PLGA-PEG-PLGA tri-block copolymer at a concentration of 8-15% w/w. The composition can comprise a PLGA-PEG-PLGA tri-block copolymer at a concentration of 8-10% w/w. The composition can comprise a PLGA-PEG-PLGA tri-block copolymer at a concentration of 5-8% w/w. The composition can comprise a PLGA-PEG-PLGA tri-block copolymer at a concentration of 8%-10% w/w. The composition can comprise a PLGA-PEG-PLGA tri-block copolymer at a concentration of 10-15% w/w. The composition can comprise a PLGA-PEG-PLGA tri-block copolymer at a concentration of 15-20% w/w. The composition can comprise a PLGA-PEG-PLGA tri-block copolymer at a concentration of 20-25% w/w.

The composition can comprise a PLGA-PEG-PLGA tri-block copolymer at a concentration of 15-20% w/w. The composition can comprise a PLGA-PEG-PLGA tri-block copolymer at a concentration of 19-20% w/w. The composition can comprise a PLGA-PEG-PLGA tri-block copolymer at a concentration of 19.1-20% w/w. The composition can comprise a PLGA-PEG-PLGA tri-block copolymer at a concentration of 19.2-20% w/w. The composition can comprise a PLGA-PEG-PLGA tri-block copolymer at a concentration of 19.5-20% w/w. The composition can comprise a PLGA-PEG-PLGA tri-block copolymer at a concentration of 19.8-20% w/w. The composition can comprise a PLGA-PEG-PLGA tri-block copolymer at a concentration of 19.0-19.5% w/w. The composition can comprise a PLGA-PEG-PLGA tri-block copolymer at a concentration of 19.0-19.2% w/w. The composition can comprise a PLGA-PEG-PLGA tri-block copolymer at a concentration of 19.2-19.5% w/w. The composition can comprise a PLGA-PEG-PLGA tri-block copolymer at a concentration of 19.5-20% w/w. The composition can comprise a PLGA-PEG-PLGA tri-block copolymer at a concentration of 25-30% w/w. The composition can comprise a PLGA-PEG-PLGA tri-block copolymer at a concentration of 30-35% w/w. The composition can comprise a PLGA-PEG-PLGA tri-block copolymer at a concentration of 25-35% w/w.

The composition can comprise a PLGA-PEG-PLGA tri-block copolymer at a concentration of 19.0% w/w. The composition can comprise a PLGA-PEG-PLGA tri-block copolymer at a concentration of 19.1% w/w. The composition can comprise a PLGA-PEG-PLGA tri-block copolymer at a concentration of 19.2% w/w. The composition can comprise a PLGA-PEG-PLGA tri-block copolymer at a concentration of 19.25% w/w. The composition can comprise a PLGA-PEG-PLGA tri-block copolymer at a concentration of 19.3% w/w. The composition can comprise a PLGA-PEG-PLGA tri-block copolymer at a concentration of 19.4% w/w. The composition can comprise a PLGA-PEG-PLGA tri-block copolymer at a concentration of 19.5% w/w. The composition can comprise a PLGA-PEG-PLGA tri-block copolymer at a concentration of 19.6% w/w. The composition can comprise a PLGA-PEG-PLGA tri-block copolymer at a concentration of 19.7% w/w. The composition can comprise a PLGA-PEG-PLGA tri-block copolymer at a concentration of 19.8% w/w. The composition can comprise a PLGA-PEG-PLGA tri-block copolymer at a concentration of 19.9% w/w. The composition can comprise a PLGA-PEG-PLGA tri-block copolymer at a concentration of 20% w/w.

The present disclosure provides a composition of funapide formulated in a PLGA-PEG-PLGA triblock copolymer, wherein the molecular weight of the PLGA polymer and PEG polymer are measured using a Gel Permeation Chromatography (GPC) method with values reported as number average (Mn).

The composition can comprise a PLGA-PEG-PLGA tri-block copolymer with each PLGA polymer block of a MW of 400 to 2550 Da. The composition can comprise a PLGA-PEG-PLGA tri-block copolymer with each PLGA polymer block of a MW of 400 to 750 Da. The composition can comprise a PLGA-PEG-PLGA tri-block copolymer with each PLGA polymer block of a MW of 750 to 1000 Da. The composition can comprise a PLGA-PEG-PLGA tri-block copolymer with each PLGA polymer block of a MW of 1000 to 1250 Da. The composition can comprise a PLGA-PEG-PLGA tri-block copolymer with each PLGA polymer block of a MW of 1250 to 1500 Da. The composition can comprise a PLGA-PEG-PLGA tri-block copolymer with each PLGA polymer block of a MW of 1500 to 1750 Da. The composition can comprise a PLGA-PEG-PLGA tri-block copolymer with each PLGA polymer block of a MW of 1750 to 2000 Da. The composition can comprise a PLGA-PEG-PLGA tri-block copolymer with each PLGA polymer block of a MW of 2000 to 2250 Da. The composition can comprise a PLGA-PEG-PLGA tri-block copolymer with each PLGA polymer block of a MW of 2250 to 2500 Da. The composition can comprise a PLGA-PEG-PLGA tri-block copolymer with each PLGA polymer block of a MW of 2500 to 2550 Da. The composition can comprise a PLGA-PEG-PLGA tri-block copolymer with each PLGA polymer block of a MW of 400 to 1000 Da. The composition can comprise a PLGA-PEG-PLGA tri-block copolymer with each PLGA polymer block blocks of a MW of 1000 to 2450 Da. The composition can comprise a PLGA-PEG-PLGA tri-block copolymer with each PLGA polymer block of a MW of 1400 to 2450 Da. The composition can comprise a PLGA-PEG-PLGA tri-block copolymer with each PLGA polymer block of a MW of 1500 to 2250 Da.

The composition can comprise a PLGA-PEG-PLGA tri-block copolymer with each PLGA polymer block of a MW of 400 Da. The composition can a PLGA-PEG-PLGA tri-block copolymer with each PLGA polymer block of a MW of 750 Da. The composition can comprise a PLGA-PEG-PLGA tri-block copolymer with each PLGA polymer block of a MW of 1000 Da. The composition can comprise a PLGA-PEG-PLGA tri-block copolymer with each PLGA polymer block of a MW of 1500 Da. The composition can comprise a PLGA-PEG-PLGA tri-block copolymer with each PLGA polymer block of a MW of 2000 Da. The composition can comprise a PLGA-PEG-PLGA tri-block copolymer with each PLGA polymer block of a MW of 2450 Da. The composition can comprise a PLGA-PEG-PLGA tri-block copolymer with each PLGA polymer block of a MW of 2550 Da.

The composition can comprise a PLGA-PEG-PLGA tri-block copolymer with the PEG polymer block of a MW of 1000-3000 Da. The composition can comprise a PLGA-PEG-PLGA tri-block copolymer with the PEG polymer block of a MW of 1000-1500 Da. The composition can comprise a PLGA-PEG-PLGA tri-block copolymer with the PEG polymer block of a MW of 1500-2000 Da. The composition can comprise a PLGA-PEG-PLGA tri-block copolymer with the PEG polymer block of a MW of 2000-2500 Da. The composition can comprise a PLGA-PEG-PLGA tri-block copolymer with the PEG polymer block of a MW of 2500-3000 Da. The composition can comprise a PLGA-PEG-PLGA tri-block copolymer with the PEG polymer block of a MW of 1000-1300 Da. The composition can comprise a PLGA-PEG-PLGA tri-block copolymer with the PEG polymer block of a MW of 1300-1600 Da. The composition can comprise a PLGA-PEG-PLGA tri-block copolymer with the PEG polymer block of a MW of 1600-1900 Da. The composition can comprise a PLGA-PEG-PLGA tri-block copolymer with the PEG polymer block of a MW of 1900-2200 Da. The composition can comprise a PLGA-PEG-PLGA tri-block copolymer with the PEG polymer block of a MW of 2200-2500 Da. The composition can comprise a PLGA-PEG-PLGA tri-block copolymer with the PEG polymer block of a MW of 2500-2750 Da. The composition can comprise a PLGA-PEG-PLGA tri-block copolymer with the PEG polymer block of a MW of 2750-3000 Da. The composition can comprise a PLGA-PEG-PLGA tri-block copolymer with the PEG polymer block of a MW of 1000-1600 Da. The composition can comprise a PLGA-PEG-PLGA tri-block copolymer with the PEG polymer block of a MW of 1400-1600 Da. The composition can comprise a PLGA-PEG-PLGA tri-block copolymer with the PEG polymer block of a MW of 1600-2000 Da. The composition can comprise a PLGA-PEG-PLGA tri-block copolymer with the PEG polymer block of a MW of 2000-2400 Da. The composition can comprise a PLGA-PEG-PLGA tri-block copolymer with the PEG polymer block of a MW of 2000-2800 Da. The composition can comprise a PLGA-PEG-PLGA tri-block copolymer with the PEG polymer block of a MW of 2800-3000 Da.

The composition can comprise a PLGA-PEG-PLGA tri-block copolymer with the PEG polymer block of a MW of 1000 Da. The composition can comprise a PLGA-PEG-PLGA tri-block copolymer with the PEG polymer block of a MW of 1250 Da. The composition can comprise a PLGA-PEG-PLGA tri-block copolymer with the PEG polymer block of a MW of 1500 Da. The composition can comprise a PLGA-PEG-PLGA tri-block copolymer with the PEG polymer block of a MW of 1850 Da. The composition can comprise a PLGA-PEG-PLGA tri-block copolymer with the PEG polymer block of a MW of 2000 D A. The composition can comprise a PLGA-PEG-PLGA tri-block copolymer with the PEG polymer block of a MW of 3000 Da.

The composition can comprise a PLGA polymer that has 40% to 100% of lactic acid (LA) and 60% to 0% of glycolic acid (GA). The composition can comprise a PLGA polymer that has 50% to 90% of lactic acid and 50% to 10% glycolic acid. The composition can comprise a PLGA polymer that has 50% to 80% of lactic acid and 50% to 20% glycolic acid. The composition can comprise a PLGA polymer that has 50% to 75% of lactic acid and 50% to 25% of glycolic acid. The composition can comprise a PLGA polymer that has 50% to 70% of lactic acid and 50% to 30% of glycolic acid. The composition can comprise a PLGA polymer that has 50% to 65% lactic acid and 50% to 35% of glycolic acid. The composition can comprise a PLGA polymer that has 50% to 60% lactic acid and 50% to 40% of glycolic acid.

The composition can comprise a PLGA polymer that has 50% of lactic acid and 50% of glycolic acid (LA:GA ratio of 50:50). The composition can comprise a PLGA polymer that has 40% of lactic acid and 60% of glycolic acid (LA:GA ratio of 40:60). The composition can comprise a PLGA polymer that has 43% of lactic acid and 57% of glycolic acid (LA:GA ratio of 43:57). The composition can comprise a PLGA polymer that has 75% of lactic acid and 25% of glycolic acid (LA:GA ratio of 75:25). The composition can comprise a PLGA polymer that has 90% of lactic acid and 10% of glycolic acid (LA:GA ratio of 90:10).

The composition can comprise a polar organic solvent that is 1-20% w/w. The composition can comprise a polar organic solvent that is 1-10.5% w/w. The composition can comprise a polar organic solvent that is 10-20% w/w. The composition can comprise a polar organic solvent that is 1-5% w/w. The composition can comprise a polar organic solvent that is 1-3% w/w. The composition can comprise a polar organic solvent that is 1-2% w/w. The composition can comprise a polar organic solvent that is 1.5-3% w/w. The composition can comprise a polar organic solvent that is 1.5-2% w/w.

The composition can comprise a polar organic solvent that is 3% w/w. The composition can comprise a polar organic solvent that is 2.5% w/w. The composition can comprise a polar organic solvent that is 2.4% w/w. The composition can comprise a polar organic solvent that is 2.3% w/w. The composition can comprise a polar organic solvent that is 1.8% w/w. The composition can comprise a polar organic solvent that is 1.7% w/w.

The composition can comprise a polar organic solvent that is any one of Dimethyl acetamide (DMA), Dimethyl sulfoxide (DMSO), Glycofurol, and N-Methyl-2-Pyrrolidone (NMP). The composition can comprise a polar organic solvent that is DMA.

The composition can comprise a solubility enhancer that is 1-7.5% w/w. The composition can comprise a solubility enhancer that is 1-10.5% w/w. The composition can comprise a solubility enhancer that is 1-12.5% w/w. The composition can comprise a solubility enhancer that is 1-15% w/w. The composition can comprise a solubility enhancer that is 1-17.5% w/w. The composition can comprise a solubility enhancer that is 1-20% w/w. The composition can comprise a solubility enhancer that is 1.5-20% w/w. The composition can comprise a solubility enhancer that is 2-20% w/w. The composition can comprise a solubility enhancer that is 2.5-20% w/w. The composition can comprise a solubility enhancer that is 3-20% w/w. The composition can comprise a solubility enhancer that is 5-20% w/w. The composition can comprise a solubility enhancer that is 1-5% w/w. The composition can comprise a solubility enhancer that is 1-3% w/w. The composition can comprise a solubility enhancer that is 1-2% w/w. The composition can comprise a solubility enhancer that is 1-1.5% w/w. The composition can comprise a solubility enhancer that is 1.5-2% w/w. The composition can comprise a solubility enhancer that is 1.7-2% w/w. The composition can comprise a solubility enhancer that is 2-2.5% w/w. The composition can comprise a solubility enhancer that is 2-3% w/w. The composition can comprise a solubility enhancer that is 2-5% w/w. The composition can comprise a solubility enhancer that is 3-5% w/w. The composition can comprise a solubility enhancer that is 5-10% w/w. The composition can comprise a solubility enhancer that is 10-15% w/w. The composition can comprise a solubility enhancer that is 15-20% w/w. The composition can comprise a solubility enhancer that is 15-17% w/w. The composition can comprise a solubility enhancer that is 17-20% w/w. The composition can comprise a solubility enhancer that is 5-11% w/w. The composition can comprise a solubility enhancer that is 6-11% w/w. The composition can comprise a solubility enhancer that is 5-7% w/w. The composition can comprise a solubility enhancer that is 7-11% w/w. The composition can comprise a solubility enhancer that is 7-9% w/w. The composition can comprise a solubility enhancer that is 8-11% w/w. The composition can comprise a solubility enhancer that is 9-11% w/w. The composition can comprise a solubility enhancer that is 10-11% w/w. The composition can comprise a solubility enhancer that is 11-15% w/w. The composition can comprise a solubility enhancer that is 11-13% w/w. The composition can comprise a solubility enhancer that is 13-16% w/w. The composition can comprise a solubility enhancer that is 16-19% w/w. The composition can comprise a solubility enhancer that is 19-20% w/w.

The composition can comprise a solubility enhancer that is 1.7% w/w. The composition can comprise a solubility enhancer that is 5% w/w. The composition can comprise a solubility enhancer that is 6% w/w. The composition can comprise a solubility enhancer that is 6.2% w/w. The composition can comprise a solubility enhancer that is 6.4% w/w. The composition can comprise a solubility enhancer that is 6.5% w/w. The composition can comprise a solubility enhancer that is 8.3% w/w. The composition can comprise a solubility enhancer that is 8.4% w/w. The composition can comprise a solubility enhancer that is 8.6% w/w. The composition can comprise a solubility enhancer that is 8.7% w/w. The composition can comprise a solubility enhancer that is 8.8% w/w. The composition can comprise a solubility enhancer that is 8.9% w/w. The composition can comprise a solubility enhancer that is 9.1% w/w. The composition can comprise a solubility enhancer that is 9.2% w/w. The composition can comprise a solubility enhancer that is 9.4% w/w. The composition can comprise a solubility enhancer that is 9.6% w/w. The composition can comprise a solubility enhancer that is 10% w/w. The composition can comprise a solubility enhancer that is 10.3% w/w. The composition can comprise a solubility enhancer that is 10.4% w/w. The composition can comprise a solubility enhancer that is 10.5% w/w. The composition can comprise a solubility enhancer that is 10.6% w/w. The composition can comprise a solubility enhancer that is 11% w/w.

The composition can comprise a solubility enhancer that is any one of Propylene glycol (PG), Cremophor EL, Cremophor RH 60, Ethanol, Glycerin, PEG 300, PEG 400, Polysorbates, Vitamin E-TPGS, PLGA-PEG diblock copolymers, hydroxypropyl-3-cyclodextrin, sulfobutyl ether-β-cyclodextrin, poloxamer 188, poloxomer 407, polyvinyl pyrrolidone (PVP), glycerol formal, and Solutol HS. The composition can comprise a solubility enhancer that is PEG 400. The composition can comprise a solubility enhancer that is polysorbate 80.

The composition can comprise a total molecular weight of the total tri-block polymer system that is between 2000-7000 Da. The composition can comprise a total molecular weight of the total tri-block polymer system that is between 2500-

7000 Da. The composition can comprise a total molecular weight of the total tri-block polymer system that is between 3000-7000 Da. The composition can comprise a total molecular weight of the total tri-block polymer system that is between 3500-7000 Da. The composition can comprise a total molecular weight of the total tri-block polymer system that is between 4000-7000 Da. The composition can comprise a total molecular weight of the total tri-block polymer system that is between 4000-5000 Da. The composition can comprise a total molecular weight of the total tri-block polymer system that is between 5000-6000 Da. The composition can comprise a total molecular weight of the total tri-block polymer system that is between 6000-7000 Da. The composition can comprise a total molecular weight of the total tri-block polymer system that is between 5000-7000 Da. The composition can comprise a total molecular weight of the total tri-block polymer system that is between 2600-6400 Da. The composition can comprise a total molecular weight of the total tri-block polymer system that is between 4300-6400 Da. The composition can comprise a total molecular weight of the total tri-block polymer system that does not exceed more than 6600-7000 Da. The composition can comprise a total molecular weight of the total tri-block polymer system that is 6000 Da. The composition can comprise a total molecular weight of the total tri-block polymer system that is less than 6000 Da.

The composition can comprise a PLGA-PEG-PLGA that is 400 Da-3000 Da-400 Da. The composition can comprise a PLGA-PEG-PLGA that is 400 Da-3050 Da-400 Da. The composition can comprise a PLGA-PEG-PLGA that is 750 Da-1850 Da-750 Da. The composition can comprise a PLGA-PEG-PLGA that is 750 Da-2500 Da-750 Da. The composition can comprise a PLGA-PEG-PLGA that is 1000 Da-1000 Da. The composition can comprise a PLGA-PEG-PLGA that is 1500 Da-1500 Da. The composition can comprise a PLGA-PEG-PLGA that is 2000 Da-2000 Da. The composition can comprise a PLGA-PEG-PLGA that is 2550 Da-1550 Da-2550 Da.

The composition can comprise a PLGA-PEG-PLGA that is 2450 Da-1500 Da-2450 Da. The composition can comprise a PLGA-PEG-PLGA that is 1700 Da-1500 Da-1700 Da. The composition can comprise a PLGA-PEG-PLGA that is 1600 Da-1500 Da-1600 Da. The composition can comprise a PLGA-PEG-PLGA that is 1600 Da-1000 Da-1600 Da.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19-19.5% w/w; (i) wherein each PLGA polymer block has a MW of 1500 Da-2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 0.65% w/w; b) a PLGA-PEG-PLGA triblock copolymer at a concentration of 19-19.5% w/w; (i) wherein each PLGA polymer block has a MW of 1500 Da-2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19% w/w; (i) wherein each PLGA polymer block has a MW of 1500 Da-2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19.2% w/w; (i) wherein each PLGA polymer block has a MW of 1500 Da-2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19.5% w/w; (i) wherein each PLGA polymer block has a MW of 1500 Da-2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19% w/w; (i) wherein each PLGA polymer block has a MW of 1500 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10% w/w.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19.2% w/w; (i) wherein each PLGA polymer block has a MW of 1500 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG-400 at a concentration of 10% w/w.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19.5% w/w; (i) wherein each PLGA polymer block has a MW of 1500 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10% w/w.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19.0 to 19.5% w/w; (i) wherein each PLGA polymer block has a MW of 2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19 to 19.2% w/w; (i) wherein each PLGA polymer block has a MW of 2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19 to 19.5% w/w; (i) wherein each PLGA polymer block has a MW of 2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 0.65% w/w; b) a PLGA-PEG-PLGA triblock copolymer at a concentration of 19% w/w; (i) wherein each PLGA polymer block has a MW of 1500-2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 0.65% w/w; b) a PLGA-PEG-PLGA triblock copolymer at a concentration of 19.2% w/w; (i) wherein each PLGA polymer block has a MW of 1500-2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 0.65% w/w; b) a PLGA-PEG-PLGA triblock copolymer at a concentration of 19.5% w/w; (i) wherein each PLGA polymer block has a MW of 1500-2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 0.65% w/w; b) a PLGA-PEG-PLGA triblock copolymer at a concentration of 19% w/w; (i) wherein each PLGA polymer block has a MW of 1500 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 0.65% w/w; b) a PLGA-PEG-PLGA triblock copolymer at a concentration of 19.2% w/w; (i) wherein each PLGA polymer block has a MW of 1500 Da, and wherein the PEG polymer has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 0.65% w/w; b) a PLGA-PEG-PLGA triblock copolymer at a concentration of 19.5% w/w; (i) wherein each PLGA polymer block has a MW of 1500 Da, and wherein the PEG polymer has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10.5% w/w.

The present disclosure provides a composition of funapide formulated in a PLGA-PEG-PLGA triblock copolymer, wherein the composition comprises: a) funapide at a concentration of 0.65% w/w; b) a PLGA-PEG-PLGA triblock copolymer at a concentration of 19% w/w; (i) wherein each PLGA polymer block has a MW of 2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10% w/w.

The present disclosure provides a composition of funapide formulated in a PLGA-PEG-PLGA triblock copolymer, wherein the composition comprises: a) funapide at a concentration of 0.65% w/w; b) a PLGA-PEG-PLGA triblock copolymer at a concentration of 19.2% w/w; (i) wherein each PLGA polymer block has a MW of 2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10%/o w/w.

The present disclosure provides a composition of funapide formulated in a PLGA-PEG-PLGA triblock copolymer, wherein the composition comprises: a) funapide at a concentration of 0.65% w/w; b) a PLGA-PEG-PLGA triblock copolymer at a concentration of 19.5% w/w; (i) wherein each PLGA polymer block has a MW of 2250 Da, and wherein the PEG polymer block has a MW of 1500 Da; and (ii) wherein the PLGA comprises 50% of lactic acid (LA) and 50% of glycolic acid (GA) (LA:GA ratio of 50:50); c) DMA at a concentration of 1.7% w/w; and d) PEG 400 at a concentration of 10% w/w.

The present disclosure provides a composition of funapide formulated in a PLGA-PEG-PLGA triblock copolymer, wherein the composition comprises: a) funapide at a concentration of 1.3% w/w; b) a PLGA-PEG-PLGA triblock copolymer at a concentration of 19-19.5% w/w; (i) wherein each PLGA polymer block has a MW of 1500 Da-2250 Da, and wherein the PEG polymer block has a MW of 1500 Da; and (ii) wherein the PLGA comprises 50% of lactic acid (LA) and 50% of glycolic acid (GA) (LA:GA ratio of 43:57); c) DMA at a concentration of 1.7% w/w; and d) PEG 400 at a concentration of 10.5% w/w.

The molecular weights of the polymer components, PLGA and PEG of the tri-block polymer of the composition as disclosed herein can be reported as weight average (Mw) and Number average (Mn). For consistency and clarity, Molecular Weights reported herein are reported as Mn as measured by Gel Permeation Chromatography (GPC). Polymer molecular weight, when measured by GPC can vary substantially based on method and system differences, including instrument manufacturers, column types and manufacturers, reagents, lab environments and standards used.

The composition can have a dose volume of 0.5 ml to 50 ml (or any integer therein). The composition can have a dose volume of 1 ml to 50 ml (or any integer therein). The composition can have a dose volume of 5 ml to 40 ml (or any integer therein). The composition can have a dose volume of 5 ml to 10 ml (or any integer therein). The composition can have a dose volume of 10 ml to 20 ml (or any integer therein). The composition can have a dose volume of 20 ml to 30 ml (or any integer therein). The composition can have a dose volume of 30 ml to 40 ml (or any integer therein). The total dose volume of the composition can be 0.5 ml. The total dose volume of the composition can be 1 ml. The total dose volume of the composition can be 5 ml. The total dose volume of the composition can be 10 ml. The total dose volume of the composition can be 15 ml. The total dose volume of the composition can be 20 ml. The total dose volume of the composition can be 25 ml. The total dose volume of the composition can be 30 ml. The total dose volume of the composition can be 35 ml. The total dose volume of the composition can be 40 ml.

The present disclosure provides a composition of funapide formulated in a PCL-PEG-PCL triblock copolymer. The present disclosure provides a composition of funapide formulated in a PDLLA-PEG-PDLLA triblock copolymer, which is the same as PLGA-PEG-PLGA where the PLGA comprises 100% of lactic acid (LA) and 0% of glycolic acid (GA) (LA:GA ratio of 100:0).

The present disclosure provides a method of treatment for post-surgical pain in a subject in need thereof, wherein the method comprises administering an effective amount of any funapide composition of the disclosure to the subject prior to, during or following a surgical procedure.

The method of treatment can comprise administering an effective amount of any funapide composition of the disclosure to the subject prior to a surgical procedure. The method of treatment can comprise administering an effective amount of any funapide composition of the disclosure to the subject 1 minute to 8 hours prior to a surgical procedure. The method of treatment can comprise administering an effective amount of any funapide composition of the disclosure to the subject 15 minutes to 8 hours prior to a surgical procedure. The method of treatment can comprise administering an effective amount of any funapide composition of the disclosure to the subject 30 minutes to 8 hours prior to a surgical procedure. The method of treatment can comprise administering an effective amount of any funapide composition of the disclosure to the subject 1 to 8 hours prior to a surgical procedure. The method of treatment can comprise administering an effective amount of any funapide composition of the disclosure to the subject 1 to 6 hours prior to a surgical procedure. The method of treatment can comprise administering an effective amount of any funapide composition of the disclosure to the subject 1 to 3 hours prior to a surgical procedure. The method of treatment can comprise administering an effective amount of any funapide composition of the disclosure to the subject 1 to 4 hours prior to a surgical procedure. The method of treatment can comprise administering an effective amount of any funapide composition of the disclosure to the subject 1 to 2 hours prior to a surgical procedure. The method of treatment can comprise administering an effective amount of any funapide composition of the disclosure to the subject 2 to 4 hours prior to a surgical procedure. The method of treatment can comprise administering an effective amount of any funapide composition of the disclosure to the subject 4 to 6 hours prior to a surgical procedure. The method of treatment can comprise administering an effective amount of any funapide composition of the disclosure to the subject 6 to 8 hours prior to a surgical procedure. The method of treatment can comprise administering an effective amount of any funapide composition of the disclosure to the subject 1 minutes, 15 minutes, 30 minutes or 1, 2, 3, 4, 5, 6, 7 or 8 hours prior to a surgical procedure.

The method of treatment can comprise administering an effective amount of any funapide composition of the disclosure to the subject during a surgical procedure.

The method of treatment can comprise administering an effective amount of any funapide composition of the disclosure to the subject following a surgical procedure. The method of treatment can comprise administering an effective amount of any funapide composition of the disclosure to the subject 1 minute-240 hours following a surgical procedure. The method of treatment can comprise administering an effective amount of any funapide composition of the disclosure to the subject 15 minutes-240 hours following a surgical procedure. The method of treatment can comprise administering an effective amount of any funapide composition of the disclosure to the subject 30 minutes-240 hours following a surgical procedure. The method of treatment can comprise administering an effective amount of any funapide composition of the disclosure to the subject 1-240 hours following a surgical procedure. The method of treatment can comprise administering an effective amount of any funapide composition of the disclosure to the subject 1 to 8 hours following a surgical procedure. The method of treatment can comprise administering an effective amount of any funapide composition of the disclosure to the subject 1 to 6 hours following a surgical procedure. The method of treatment can comprise administering an effective amount of any funapide composition of the disclosure to the subject 1 to 3 hours following a surgical procedure. The method of treatment can comprise administering an effective amount of any funapide composition of the disclosure to the subject 1 to 4 hours following a surgical procedure. The method of treatment can comprise administering an effective amount of any funapide composition of the disclosure to the subject 1 to 2 hours following a surgical procedure. The method of treatment can comprise administering an effective amount of any funapide composition of the disclosure to the subject 2 to 4 hours following a surgical procedure. The method of treatment can comprise administering an effective amount of any funapide composition of the disclosure to the subject 4 to 6 hours following a surgical procedure. The method of treatment can comprise administering an effective amount of any funapide composition of the disclosure to the subject 6 to 8 hours following a surgical procedure. The method of treatment can comprise administering an effective amount of any funapide composition of the disclosure to the subject 8 to 10 hours following a surgical procedure. The method of treatment can comprise administering an effective amount of any funapide composition of the disclosure to the subject 10 to 12 hours following a surgical procedure. The method of treatment can comprise administering an effective amount of any funapide composition of the disclosure to the subject 12 to 24 hours following a surgical procedure. The method of treatment can comprise administering an effective amount of any funapide composition of the disclosure to the subject 24 to 48 hours following a surgical procedure. The method of treatment can comprise administering an effective amount of any funapide composition of the disclosure to the subject 48 to 72 hours following a surgical procedure. The method of treatment can comprise administering an effective amount of any funapide composition of the disclosure to the subject 72 to 96 hours following a surgical procedure. The method of treatment can comprise administering an effective amount of any funapide composition of the disclosure to the subject 96 to 120 hours following a surgical procedure. The method of treatment can comprise administering an effective amount of any funapide composition of the disclosure to the subject 120 to 144 hours following a surgical procedure. The method of treatment can comprise administering an effective amount of any funapide composition of the disclosure to the subject 144 to 168 hours following a surgical procedure. The method of treatment can comprise administering an effective amount of any funapide composition of the disclosure to the subject 168 to 192 hours following a surgical procedure. The method of treatment can comprise administering an effective amount of any funapide composition of the disclosure to the subject 192 to 216 hours following a surgical procedure. The method of treatment can comprise administering an effective amount of any funapide composition of the disclosure to the subject 216 to 240 hours following a surgical procedure. The method of treatment can comprise administering an effective amount of any funapide composition of the disclosure to the subject 1 minute, 15 minutes, 30 minutes or 1, 2, 3, 4, 5, 6, 7, 8, 9, 10, 12, 24, 48, 72, 96, 120, 144, 168, 192, 216 or 240 hours following a surgical procedure.

The method of treatment can comprise administering an effective amount of any funapide composition of the disclosure to the subject prior to surgical procedure and an effective amount of any funapide composition of the disclosure to the subject following a surgical procedure. The method of treatment can comprise administering an effective amount of any funapide composition of the disclosure to the subject 1 minute to 1 hour or 1 to 8 hours prior to a surgical procedure, and administering an effective amount of any funapide composition of the disclosure to the subject 1 minute to 1 hour or 1 to 240 hours following the surgical procedure.

The method of treatment can comprise administering an effective amount of any funapide composition of the disclosure to the subject 1 to 6 hours prior to a surgical procedure, and administering an effective amount of any funapide composition of the disclosure to the subject 1 to 240 hours following the surgical procedure. The method of treatment can comprise administering an effective amount of any funapide composition of the disclosure to the subject 1 to 3 hours prior to a surgical procedure, and administering an effective amount of any funapide composition of the disclosure to the subject 1 to 240 hours following the surgical procedure. The method of treatment can comprise administering an effective amount of any funapide composition of the disclosure to the subject 1 to 4 hours prior to a surgical procedure, and administering an effective amount of any funapide composition of the disclosure to the subject 1 to 240 hours following the surgical procedure. The method of treatment can comprise administering an effective amount of any funapide composition of the disclosure to the subject 1 to 2 hours prior to a surgical procedure, and administering an effective amount of any funapide composition of the disclosure to the subject 1 to 240 hours following the surgical procedure. The method of treatment can comprise administering an effective amount of any funapide composition of the disclosure to the subject 2 to 4 hours prior to a surgical procedure, and administering an effective amount of any funapide composition of the disclosure to the subject 1 to 240 hours following the surgical procedure. The method of treatment can comprise administering an effective amount of any funapide composition of the disclosure to the subject 4 to 6 hours prior to a surgical procedure, and administering an effective amount of any funapide composition of the disclosure to the subject 1 to 240 hours following the surgical procedure. The method of treatment can comprise administering an effective amount of any funapide composition of the disclosure to the subject 6 to 8 hours prior to a surgical procedure, and administering an effective amount of any funapide composition of the disclosure to the subject 1 to 240 hours following the surgical procedure. The method of treatment can comprise administering an effective amount of any funapide composition of the disclosure to the subject 1 minute, 15 minutes, 30 minutes or 1, 3, 3, 4, 5, 6, 7 or 8 hours prior to a surgical procedure, and administering an effective amount of any funapide composition of the disclosure to the subject 1 minute, 15 minutes, 30 minutes or 1 to 240 hours following the surgical procedure.

The method of treatment can comprise administering an effective amount of any funapide composition of the disclosure to the subject 1 minute to 1 hour or 1 to 8 hours prior to a surgical procedure, and administering an effective amount of any funapide composition of the disclosure to the subject 1 minute to 1 hour or 1 to 240 hours following the surgical procedure. The method of treatment can comprise administering an effective amount of any funapide composition of the disclosure to the subject 1 to 8 hours prior to a surgical procedure, and administering an effective amount of any funapide composition of the disclosure to the subject 1 to 8 hours following the surgical procedure. The method of treatment can comprise administering an effective amount of any funapide composition of the disclosure to the subject 1 to 8 hours prior to a surgical procedure, and administering an effective amount of any funapide composition of the disclosure to the subject 1 to 6 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 1 to 4 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 1 to 3 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 1 to 2 hours following a surgical procedure following the surgical procedure.

The method of treatment can comprise administering an effective amount of any funapide composition of the disclosure to the subject 1 minute to 1 hour or 1 to 8 hours prior to a surgical procedure, and administering an effective amount of any funapide composition of the disclosure to the subject 1 minute to 2 hours or 2 to 4 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 4 to 6 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 6 to 8 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 8 to 10 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 10 to 12 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 12 to 24 hours following a surgical procedure following the surgical procedure.

The method of treatment can comprise administering an effective amount of any funapide composition of the disclosure to the subject 1 to 8 hours prior to a surgical procedure, and administering an effective amount of any funapide composition of the disclosure to the subject 24 to 48 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 48 to 72 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 71 to 96 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 96 to 120 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 122 to 144 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 144 to 168 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 168 to 192 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 192 to 216 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 216 to 240 hours following a surgical procedure following the surgical procedure. The method of treatment can comprise administering an effective amount of any funapide composition of the disclosure to the subject 1 to 8 hours prior to a surgical procedure, and administering an effective amount of any funapide composition of the disclosure to the subject 1 minute, 15 minutes, 30 minutes or 1, 2, 3, 4, 5, 6, 7, 8, 9, 10, 12, 24, 48, 72, 96, 120, 144, 168, 192, 216 or 240 hours following a surgical procedure following the surgical procedure.

The present disclosure provides a method of treatment for pain in a subject in need thereof, wherein the method comprises administering to the subject an effective amount of any of the compositions disclosed herein. The pain can be acute pain. The acute pain can be due to any one of an injury, dental work or labor and childbirth, or any combination thereof. The term "acute pain" is used herein in its broadest sense to refer to pain that has a duration of less than 6 months, preferably less than 3 months. As would be appreciated by the skilled artisan, acute pain can be attributed to a specific cause (e.g. injury, dental work, labor and childbirth, etc.) and typically subsides after the specific cause is treated.

The method of treatment can comprise administering an effective amount of any funapide composition of the disclosure to the subject wherein the effective amount induces an analgesic nerve block. The effective amount induces an analgesic nerve block prior to surgical procedure. The effective amount induces an analgesic nerve block during a surgical procedure. The effective amount induces an analgesic nerve block following a surgical procedure. The effective amount induces an analgesic nerve block following an injury. The effective amount induces an analgesic nerve block following a surgical procedure. The effective amount induces an analgesic nerve block prior to dental work. The effective amount induces an analgesic nerve block during dental work. The effective amount induces an analgesic nerve block during labor and childbirth, including Cesarean delivery if required.

The analgesic nerve block can be any one of upper extremity nerve block, lower extremity nerve block, facial nerve block, neck and back nerve block, chest and abdominal block, or any combination thereof. The upper extremity nerve block can be any one of interscalene, supraclavicular, brachial plexus and infraclavicular nerve block, or any combination thereof. The lower extremity nerve block can be any one of hypogastric plexus, lumbar plexus, femoral nerve, adductor canal nerves, popliteal fossa and sciatic nerve, or any combination thereof. The facial nerve block can be any one of trigeminal, ophthalmic, supraorbital, maxillary, sphenopalatine, or any combination thereof. The neck and back nerve block can be any one of cervical epidural, thoracic epidural, lumbar epidural, caudal block or any combination thereof. The chest and abdominal block can be any one of paravertebral, intercostal and transversus abdominis plane, rectus sheath or any combination thereof.

The surgical procedure can be any one of diagnostic surgical procedure, ablative surgical procedure, palliative surgical procedure, reconstructive surgical procedure, transplantation surgical procedure, constructive surgical procedure, or any combination thereof.

The surgical procedure can be any one of upper extremity surgical procedure, lower extremity surgical procedure, abdominal surgical procedure, cardio-thoracic surgical procedure, head and neck surgical procedure, back surgical procedure, musculoskeletal surgical procedure, orthopedic surgical procedure, ocular surgical procedure, ear, nose and throat surgical procedure, vascular surgical procedure, dental surgical procedure, or any combination thereof.

The surgical procedure can be any one of upper extremity surgical procedure and lower extremity surgical procedure, or any combination thereof. The upper extremity surgical procedure can be any one of a surgical procedure of arm, forearm, hand, wrist, elbow, shoulder, or any combination thereof. The upper extremity surgical procedure can be a surgical procedure of one or more bone(s) of the arm, forearm, hand, wrist, elbow, shoulder, or any combination thereof. The one or more bone(s) can comprise any one of radius, ulna, humerus, carpals, metacrapals or phalanges or a combination thereof.

The elbow and shoulder surgical procedure can be any one of a fracture surgery, total shoulder replacement, reverse shoulder replacement, shoulder arthroscopy, elbow arthroscopy, rotator cuff repair, surgery for tennis and golfer's elbow, or any combination thereof. The hand and wrist surgical procedure can be any one of a fracture surgery, carpal tunnel release, wrist arthroscopy, wrist joint replacement, wrist fusion, or any combination thereof.

The lower extremity surgical procedure is any one of a surgical procedure of hip, thigh, knee, ankle, feet, or any combination thereof. The lower extremity surgical procedure can be a surgical procedure of one or more bone(s) of the hip, thigh, knee, ankle, feet, or any combination thereof. The one or more bone(s) can comprise any one of acetabulum, femur, tibia, fibula, patella, tarsal bone, metatarsal bone, arches of the foot or a combination thereof.

The lower extremity surgical procedure can be any one of arthroscopy (diagnostic tool and treatment method to see inside joints), bone fusion, open-reduction fracture setting, surgical removal (i.e. of bunions, cysts, nail, etc.), tendon and ligament repair or any combination thereof.

The abdominal surgical procedure can be any one of a surgical procedure of the stomach, small intestines, spleen, appendix and the colon (or rectum). The abdominal surgical procedure can be any one of appendectomy, cholecystectomy, colon/anorectal surgery, colon/large bowel resections, hernia surgery, small bowel resection, or any combination thereof.

The cardio-thoracic surgical procedure can be any one of a surgical procedure of the lung or heart. The cardio-thoracic surgical procedure can be any one of a surgical procedure of the respiratory system, the cardiovascular system, or any combination thereof. The cardio-thoracic surgical procedure can be any one of thoracotomy, lobectomy, pneumonectomy, lung transplant, surgery to prevent pleurodesis, surgery to prevent empyema, surgery to remove blood in the chest cavity (particularly after trauma heart transplant), surgery to remove small balloon-like tissues (blebs) that cause lung collapse (pneumothorax), wedge resection, aortic surgery, atrial fibrillation surgery (hybrid-maze procedure), carotid endarterectomy, coronary artery bypass surgery (CABG), heart valve repair/replacement surgery, heart valve replacement without surgery, mitral valve repair, minimally invasive cardiac surgery, robotic thoracic surgery, or any combination thereof.

The head and neck surgical procedure can be any one of a surgery for pinched nerves, intense dizziness and motion sickness, pressure on spinal cord, upper spinal issues, head and neck injuries, sinus pain, chronic ear infections, snoring and sleep apnea, tonsil issues, jaw issues and deformities, thyroid conditions, or any combination thereof.

The back surgical procedure can be a surgical procedure for correcting or repairing defects or injuries of the vertebral column. The back surgical procedures can be any one of a surgical procedure for correction or repair of herniated or ruptured disks, spinal stenosis, spondylolisthesis, vertebral fractures, degenerative disk disease, or any combination thereof.

The orthopedic surgical procedure can be any one of arthroscopy, soft tissue repair, joint replacement, revision joint surgery, bone fracture repair, debridement, fusion of bones, spine fusion, osteotomy, or any combination thereof. The orthopedic surgical procedure can be any one of knee arthroscopy and meniscectomy, shoulder arthroscopy and decompression, carpal tunnel release, knee arthroscopy and chondroplasty, removal of support implant, knee arthroscopy and anterior cruciate ligament reconstruction, knee replacement, repair of femoral neck fracture, repair of trochanteric fracture, hip replacement, or any combination thereof.

The ocular surgical procedure can be any one of oculoplastic surgery, surgical procedure of cornea, retina and eye muscle, refractive surgery, glaucoma surgery, or any combination thereof.

The vascular surgical procedure can be any one of aortic aneurysm repair aortocaval fistula repair, aortoenteric fistula repair, arteriovenous fistula surgery, arteriovenous malformation surgery, bypass surgery, carotid angioplasty and stenting, carotid artery stenting, carotid endarterectomy, celiac artery bypass, coronary angioplasty and stents, endovascular reconstruction, endovenous laser therapy, ex vivo renal artery reconstructions, inferior vena cava (ivc) filter retrieval, inferior vena cava (ivc) placement, laser ablation, mesenteric artery bypass, open vascular reconstruction, radiofrequency ablation, renal artery angioplasty, renal artery bypass, renal artery endarterectomy, stenting to repair aneurysms, subfascial endoscopic perforator surgery, thoracic duct embolization, thoracic outlet decompression, thrombectomy, vascular stenting, vein removal, vena cava reconstructions, vertebral artery reconstructions, or any combination thereof.

The dental surgical procedure can be any one of endodontics, root canal surgery, apicoectomy, prosthodontic surgery, orthodontic surgery, periodontic surgery, oral and maxillofacial surgery, or any combination thereof.

The surgical procedure can be of any one of an abdominal wall, a thoracic wall or a combination thereof. The surgical procedure of the abdominal wall can be a surgical procedure for abdominal wall reconstruction and repair. The surgical procedure of the abdominal wall can be a surgical procedure for abdominal wall hernia.

The surgical procedure can be a surgical procedure of an organ. The organ can be any one of heart, lung, liver, spleen, brain, stomach, small intestine, large intestine, gall bladder, bile ducts, lymphatic ducts, urinary bladder, prostate gland, pancreas, adrenal gland, thyroid gland, skin, uterus, fallopian tubes, ovary, seminal tubules, testes, or any combination thereof. The surgical procedure can be for any one of repair, removal or transplantation of the organ. The organ surgical procedure can be for removal of tumor or cancerous tissue from within or near the organ.

The surgical procedure can be any one of upper extremity surgical procedure and lower extremity surgical procedure. The surgical procedure can be any one of bunionectomy, total knee arthroplasty, anterior cruciate ligament reconstruction, shoulder arthroplasty (total or reverse), rotator cuff repair or a combination thereof.

The subject in need thereof, can be a subject that is to undergo, is undergoing or has undergone a surgical procedure can be a human. The subject can be a mammal. The subject can be a human, a murine, an equine, a canine, a feline, a rabbit, a pig, a hamster, a bovine or a camelid. The subject can be a human.

The effective amount of the composition can be administered perineurally, epidurally, subcutaneously, intradermally, orally, intramuscularly or intravenously. The effective amount of the formulation can be administered perineurally. The effective amount of the formulation is administered by direct instillation into a wound near the site of surgical procedure. The effective amount of the formulation is administered by the effective amount of the formulation is administered by infiltration at the site of surgical procedure.

Dosage

The disclosure provides an effective amount of the composition of the disclosure, for use in a method for managing pain in a subject in need thereof, caused by an injury, wound or surgical procedure while not materially impairing motor function. Managing pain can be defined as any one or all of: a) reducing pain intensity, and b) preventing need to or increasing the time to administer rescue anti-pain medication post-administration of the composition.

Managing pain can be defined as reducing the pain intensity in a subject that has undergone injury, wound or surgical procedure as measured on a numerical rating scale (NRS) scale. A NRS scale for assessing pain intensity of the subject in need thereof, on a defined 11-point (0-10), 21-point (0-20) and 101-point (0-100) scale (Jensen & Karoly 2001), wherein a score of 0 means "no pain", scores of 10, 20 and 100 mean "worst pain imaginable", and scores between 0 and the highest point on the scale being mild to moderate pain in ascending order. The effective amount is an amount that causes reduction of pain intensity in the subject in need thereof, as measured on a NRS scale, from a score that means "worst pain imaginable" on Day 0 post-surgery/injury, to a score that means "no pain" at a time between 24 hours to 7 days post-surgery/injury. The effective amount is an amount that causes reduction of pain intensity in the subject in need thereof, as measured on a NRS scale, from a score that means "worst pain imaginable" at Day 0 post-surgery/injury, to a score that means "mild pain" at a time between 24 hours to 7 days post-surgery/injury. The effective amount is an amount that causes reduction of pain intensity in the subject in need thereof, as measured on a NRS scale, from a score that means "worst pain imaginable" at Day 0 post-surgery/injury, to a score that means "moderate pain" at a time between 24 hours to 7 days post-surgery/injury. The effective amount is an amount that causes reduction of pain intensity in the subject in need thereof, as measured on a NRS scale, from a score that means "moderate pain" at Day 0 post-surgery/injury, to a score that means "mild pain" at a time between 24 hours to 7 days post-surgery/injury.

The "effective amount" or "therapeutically effective amount" of the composition as disclosed herein, is an amount of the composition that upon administering to a subject in need thereof, reduces or inhibits pain or makes pain manageable in the subject. The "effective amount" or "therapeutically effective amount" of the composition as disclosed herein, is an amount of the composition, that causes reduction of pain intensity in the subject in need thereof, as measured on a 11-point NRS scale, from a score of 10 at Day 0 post-surgery/injury, to a score of 0 at a time between 24 hours to 7 days post-surgery/injury. The effective amount is an amount that causes reduction of pain intensity in the subject in need thereof, as measured on a 11-point NRS scale, from a score of 10 at Day 0 post-surgery/injury, to a score of 0-5 at a time between 24 hours to 7 days post-surgery/injury. The effective amount is an amount that causes reduction of pain intensity in the subject in need thereof, as measured on a 11-point NRS scale, from a score of 8-10 at Day 0 post-surgery/injury, to a score of 5-7 at a time between 24 hours to 7 days post-surgery/injury. The effective amount is an amount that causes reduction of pain intensity in the subject in need thereof, as measured on a 11-point NRS scale, from a score of 6-10 at Day 0 post-surgery/injury, to a score of 0-5 at a time between 24 hours to 7 days post-surgery/injury.

The loss of motor function in the subject that has undergone injury, wound or surgical procedure, can be measured by assessing motor strength, specifically, strength of knee extension and flexion, ankle dorsiflexion, and ankle plantar flexion.

The preventing the need to, or increasing the time to administer rescue anti-pain medication post-administration of the composition, to the subject that has undergone injury, wound or surgical procedure, can be assessed by determining the time post-surgery/injury, for which the subject can remain without concomitant use of an anti-pain medication. The anti-pain medication can be an opioid medication. The opioid medication can be any one of or a combination of oxycodone, morphine, codeine, fentanyl, hydrocodone, meperidine and methadone. The effective amount of the composition as disclosed herein can be an amount that prevents the need for administering an opioid medication less than 1 week post surgery/injury. The effective amount of the composition as disclosed herein can be an amount that prevents the need for administering an opioid medication less than 4 weeks post surgery/injury. An effective amount of the composition as disclosed herein can be an amount that prevents the need for administering an opioid medication less than 8 weeks post surgery/injury.

The method of treatment can comprise administering an effective amount of any funapide composition of the disclosure to the subject in need thereof, wherein the effective amount of the composition can be 1-20 mg/ml. The method of treatment can comprise administering an effective amount of any funapide composition of the disclosure to the subject in need thereof, wherein the effective amount of the composition can be 1.5-20 mg/ml. The method of treatment can comprise administering an effective amount of any funapide composition of the disclosure to the subject in need thereof, wherein the effective amount of the funapide composition can be 2-20 mg/ml. The effective amount of the funapide composition can be 6-13 mg/ml. The effective amount of the composition can be 2-5 mg/ml. The effective amount of the funapide composition can be 5-10 mg/ml. The effective amount of the funapide composition can be 10-15 mg/ml. The effective amount of the funapide composition can be 15-20 mg/ml. The effective amount of the funapide composition can be 3-6 mg/ml. The effective amount of the funapide composition can be 6-13 mg/ml. The effective amount of the funapide composition can be 6.5-13 mg/ml. The effective amount of the funapide composition can be 10-13 mg/ml. The effective amount of the funapide composition can be 13-16 mg/ml. The effective amount of the funapide composition can be 16-19 mg/ml. The effective amount of the funapide composition can be 19-20 mg/ml. The effective amount of the funapide composition can be 6.5 mg/ml. The effective amount of the funapide composition can be 13 mg/ml.

The method of treatment can comprise administering an effective amount of any funapide composition of the disclosure to the subject in need thereof, wherein the effective amount of the funapide composition can be a dose volume of 5-40 ml. The effective amount of the funapide composition can be a dose volume of 5-10 ml. The effective amount of the funapide composition can be a dose volume of 10-15 ml. The effective amount of the funapide composition can be a dose volume of 15-20 ml. The effective amount of the funapide composition can be a dose volume of 20-25 ml. The effective amount of the funapide composition can be a dose volume of 25-30 ml. The effective amount of the funapide composition can be a dose volume of 30-35 ml. The effective amount of the funapide composition can be a dose volume of 35-40 ml. The effective amount of the funapide composition can be a dose volume of 10-20 ml. The effective amount of the funapide composition can be a dose volume of 20-30 ml. The effective amount of the funapide composition can be a dose volume of 30-40 ml. The effective amount of the funapide composition can be a dose volume of 5 ml. The effective amount of the funapide composition can be a dose volume of 10 ml. The effective amount of the funapide composition can be a dose volume of 20 ml. The effective amount of the funapide composition can be a dose volume of 30 ml. The effective amount of the funapide composition can be a dose volume of 40 ml. The effective amount of the funapide composition can be 6.5 mg/ml in a dose volume of 10 ml. The effective amount of the funapide composition can be 13 mg/ml in a dose volume of 20 ml.

The present disclosure provides a method of treatment for post-surgical pain in a subject in need thereof, wherein the subject can be a mammal. The present disclosure provides a method of treatment for pain in a subject in need thereof, wherein the subject can be a mammal. The subject can be a human, a murine, an equine, a canine, a feline, a rabbit, a pig, a hamster, a bovine or a camelid. The subject can be a human. The human subject can be a male. The human subject can be a female.

The effective amount of the funapide composition can be administered perineurally, epidurally, subcutaneously, intradermally, orally, intramuscularly or intravenously. The effective amount of the formulation can be administered perineurally. The effective amount of the formulation is administered by direct instillation into a wound near the site of surgical procedure. The effective amount of the formulation is administered by infiltration at the site of surgical procedure.

An ultrasound probe can be used for administering the effective amount of the funapide composition to a site near a nerve distal to the site of surgery or injury of the subject in need thereof, wherein the targeted nerve provides innervation to the site of surgery or injury, with the aid of an ultrasound guided probe.

Figure 1A:
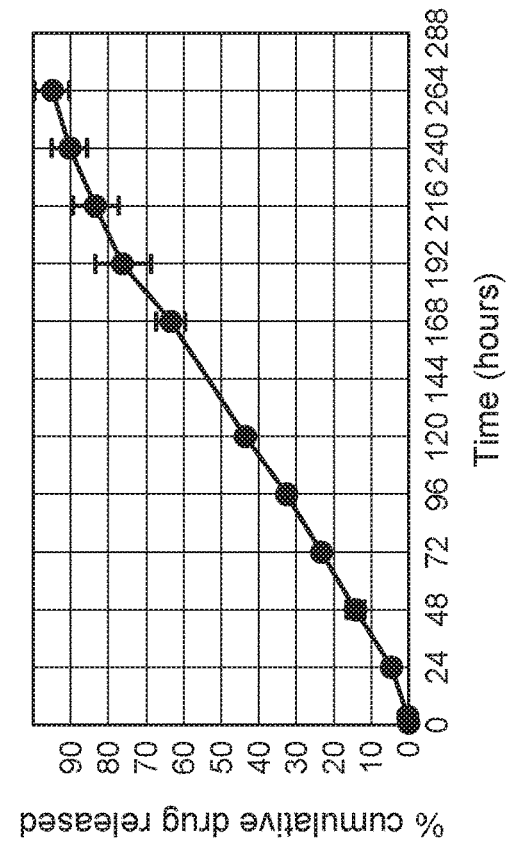
Figure 15A:
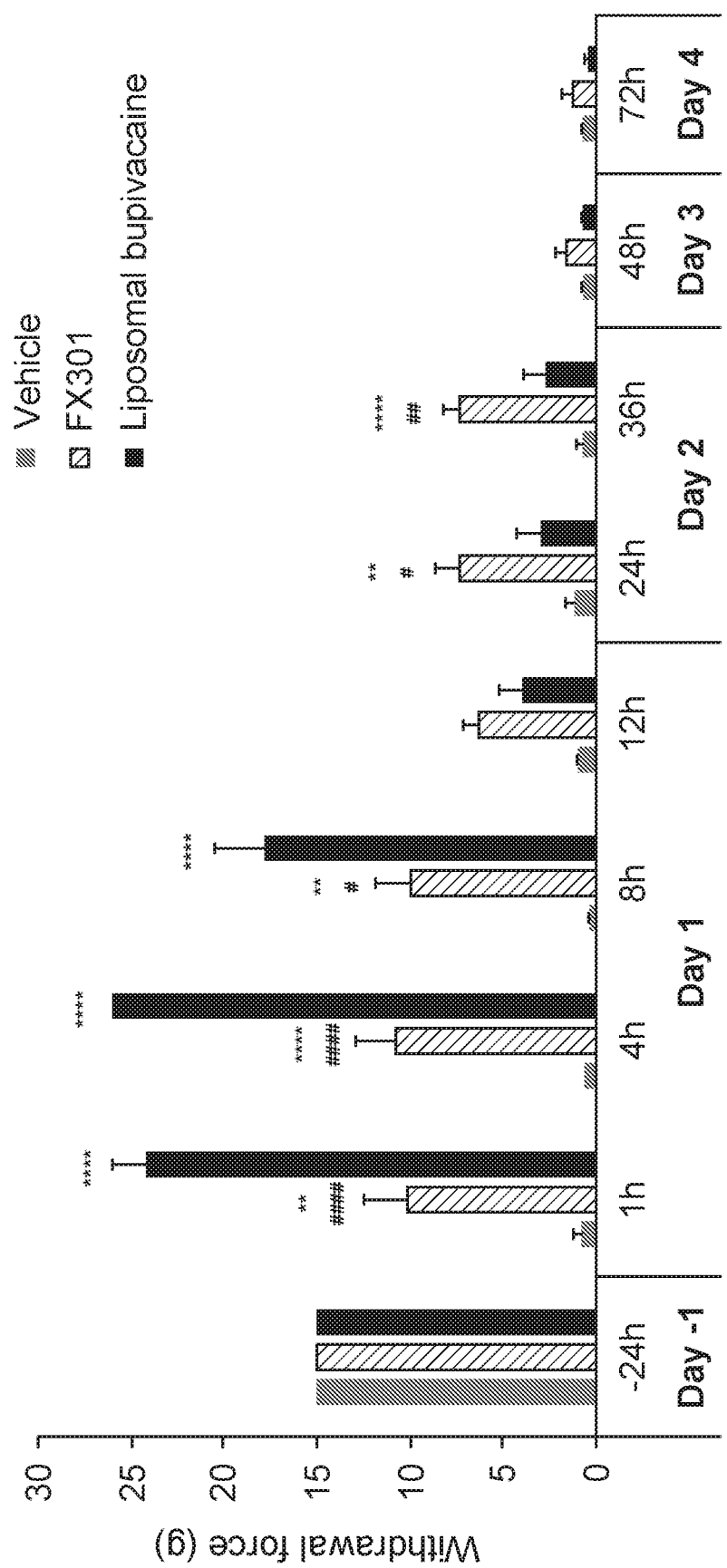
FIG. 15A-15C. Efficacy and pharmacokinetics of peripheral nerve block by FX301 in a postoperative pain model in pigs. Following habituation for 5 days, a total of 18 pigs were anesthetized and then injected with 10 mL of vehicle (n=6), FX301 (13 mg/mL; total dose 130 mg) (n=6), or liposomal bupivacaine (13.3 mg/mL; total dose 133 mg) (n=6), in close proximity to the sciatic nerve under ultrasound guidance. Surgical pain was then induced by a 5-cm long incision in the dorsal area of the ipsilateral hind leg immediately after injection.
Figure 17A:
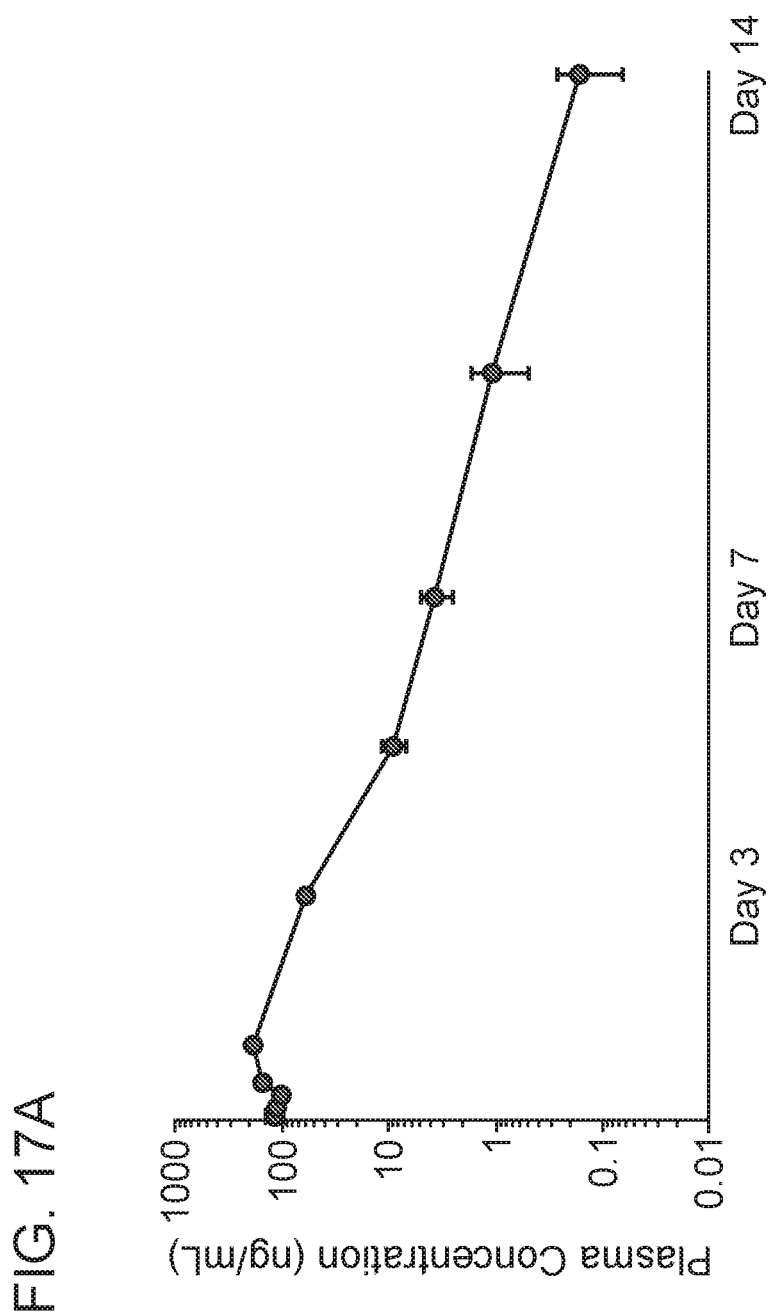
FIG. 17A-17B. FX301 delivers funapide locally for at least 3 days.
Figure 17B:
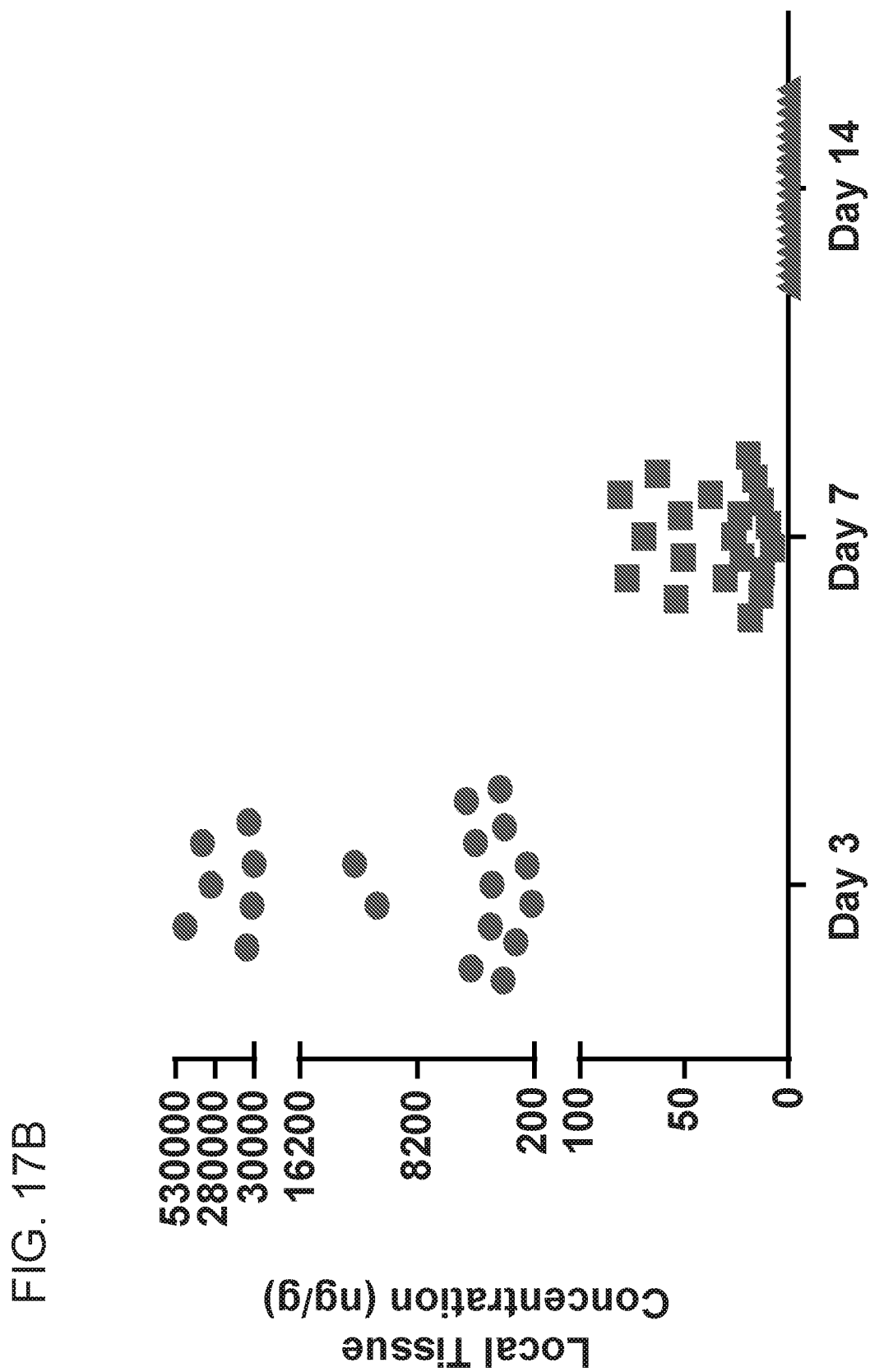

The results provided in the instant disclosure demonstrate consistent and extended release kinetics of funapide from the composition disclosed herein (FIG. 1A). The results provided in the instant disclosure demonstrate that treatment with the composition as disclosed herein, leads to a significant increase in withdrawal force with a relatively long duration of activity in subjects that have undergone surgery (FIG. 15A). After a single, perineural injection in pigs: systemic PK profile confirmed extended release of funapide from the composition (FIG. 17A). High local concentrations are maintained at the site of injection around the nerve, consistent with the analgesic profile (FIG. 17B). The results provided in the instant disclosure demonstrate that the composition as disclosed herein delivers funapide, a preferential Nav1.7 antagonist, locally for up to 7 days.

The results provided in the instant disclosure demonstrate that the composition disclosed herein increased the withdrawal threshold following surgical incision through 36 hours after injection and improved behavior scores, consistent with less pain-related behaviors, through 12 hours after injection. No impairment of motor activity was observed in subjects administered with the composition as disclosed herein, with no significant change in total walking distance at 2 and 24 hours after injection. After single administration of the composition as disclosed herein, high local funapide concentrations were present at 72 hours. The plasma profile of funapide was consistent with a slow sustained release throughout the study. These results disclosed herein support the use of the composition disclosed herein, in methods of treatment for, and management of post-surgical pain in a subject in need thereof while not materially impairing motor function.

The present disclosure provides a method of manufacturing any of the compositions disclosed herein. The method of manufacturing any of the compositions disclosed herein comprises: i) combining and dissolving: a) an amount of the PLGA-PEG-PLGA tri-block polymer; b) an amount of water; c) an amount of the funapide; d) an amount of the polar organic solvent; and e) an amount of the solubility enhancer, to form a mixture; ii) stirring the mixture of (i) at 1-30° C.; iii) filtering the clear solution of (ii) through a sterile filter; and iv) collecting and freezing the filtered solution of (iii) at ≤−20° C.

In the method of manufacturing any of the compositions disclosed herein, the dissolved funapide solution is then combined with the polymer solution to stir at 8-12° C.

The method of manufacturing any of the compositions disclosed herein, can comprise in step i): 1) compounding and dissolving the amount of the PLGA-PEG-PLGA tri-block polymer of (a) in the amount of water of (b) at 1-30° C., to form a polymer solution; 2) dissolving the amount of the funapide of (c) in the amount of the polar organic solvent of (d) and the amount of the solubility enhancer of (e), in a separate vessel to form a funapide solution; and 3) combining the dissolved funapide solution of (2) with the polymer solution of (1) to form a mixture. In the method of manufacturing any of the compositions disclosed herein, temperature of stirring the mixture can be 8-12° C.

In the method of manufacturing any of the compositions disclosed herein, the compounding and dissolving of the funapide, the PLGA-PEG-PLGA tri-block polymer, the polar organic solvent, the solubility enhancer and water is done under controlled environmental conditions compatible with incorporation into an aseptic fill-finish process. In the method of manufacturing any of the compositions disclosed herein, the sterile filter is a 0.5/0.2 μm sterile filter.

The present disclosure is further illustrated by the following examples that should not be construed as limiting. The contents of all references, patents, and published patent applications cited throughout this application, as well as the Figures, are incorporated herein by reference in their entirety for all purposes. The description will be further illustrated in the examples following below.

EXAMPLES

Example 1: Funapide-PLGA-PEG-PLGA Triblock Polymer Formulation (FX301)

One formulation of funapide formulated in a tri-block polymer of PLGA-PEG-PLGA (referred to as FX301 hereafter) is composed of 1.7% Dimethyl Acetamide (DMA)+ 10.5% Polyethylene glycol 400 (PEG 400)+19.2% Polymer+water. The polymer used in the lead formulation is 1500-1500-1500 PLGA-PEG-PLGA (LA:GA 50:50). The funapide can be loaded up to 20 mg/mL drug concentration within the thermosensitive hydrogel formulation. Described herein are the in vitro release profile of the final FX301 formulation and the systemic PK profile of the API achieved after nerve block application in post-surgical pig model (FIG. 1). The results disclosed herein, indicate a release profile consistent with controlled sustained release of Nav1.7 antagonist from the hydrogel formulation. This allows for high concentrations of drug to be released locally at the nerve to maintain target coverage over a longer period of time than can be achieved with a simple solution of drug.

Example 2: Overview of FX301 formulation Development and Optimization

Described herein is the formulation development and screening that lead to the nominated formulation focused on polymer characteristics, drug loading, and processing conditions, with over 100 unique formulations (Table 1) prepared and evaluated.

TABLE 1

Master table of all novel gel formulations prepared using Funapide

| Lot # | Target Drug Load (mg/mL) | Solvent system | Polymer system |
|---|---|---|---|
| NB-0032-002-01 | 5 | 2.5% DMA + 9% polysorbate 80 | 11% 6k PLGA-PEG-PLGA (2200-1500-2200, LA:GA 50:50) |
| NB-0032-002-02 | | | 13% 6k PLGA-PEG-PLGA (2200-1500-2200, LA:GA 50:50) |
| NB-0032-002-03 | | | 13% PLGA-PEG-PLGA (1700-1500-1700, LA:GA 75:25) |
| NB-0032-002-04 | | | 14% PLGA-PEG-PLGA (1700-1500-1700, LA:GA 75:25) |
| NB-0032-002-04S | | | 14% PLGA-PEG-PLGA (1700-1500-1700, LA:GA 75:25) |
| NB-0032-002-05 | | | 17% PLGA-PEG-PLGA (1500-1500-1500, LA:GA 50:50) |
| NB-0032-002-06 | | | 17% PLGA-PEG-PLGA (1100-1100-1100, LA:GA 75:25) |
| NB-0032-002-07 | | | 17% PLGA-PEG-PLGA (1600-1000-1600, LA:GA 50:50) |
| NB-0032-002-08 | | | 11% PLGA-PEG-PLGA (1500-1500-1500, LA:GA 50:50) + 6% PLGA-PEG-PLGA (1600-1000-1600, LA:GA 50:50) |
| NB-0032-003-04 | 5 | 6.5% PEG400 + 9% polysorbate 80 | 13% PLGA-PEG-PLGA (1700-1500-1700, LA:GA 75:25) |
| NB-0032-003-05 | | | 14% PLGA-PEG-PLGA (1700-1500-1700, LA:GA 75:25) |
| NB-0032-003-06 | | | 16% PLGA-PEG-PLGA (1500-1500-1500, LA:GA 50:50) |
| NB-0032-003-07 | | | 16% PLGA-PEG-PLGA (1100-1100-1100, LA:GA 75:25) |
| NB-0032-003-10 | | | 16% PLGA-PEG-PLGA (1600-1000-1600, LA:GA 50:50) |
| NB-0032-003-08 | | | 8% PLGA-PEG-PLGA (1500-1500-1500, LA:GA 50:50) + 8% PLGA-PEG-PLGA (1600-1000-1600, LA:GA 50:50) |
| NB-0032-004-03 | 5 | 6.5% PEG400 + 9% polysorbate 80 | 10% PLGA-PEG-PLGA (2200-1500-2200, LA:GA 50:50) |
| NB-0032-004-04 | | | 12% 6k PLGA-PEG-PLGA (2200-1500-2200, LA:GA 50:50) |
| NB-0032-010-02 | 5 | 2.5% DMA + 9% polysorbate 80 | 11% PLGA-PEG-PLGA (1700-1500-1700, LA:GA 75:25) |
| NB-0032-016-04 | | 6% PEG 400 + 9% polysorbate 80 | 16% PLGA-PEG-PLGA (1500-1500-1500, LA:GA 50:50) |
| NB-0032-016-05 | 5 | 2.5% DMA + 9% polysorbate 80 | 11% PLGA-PEG-PLGA (1700-1500-1700, LA:GA 75:25) |
| NB-0032-016-06 | | 6% PEG400 + 9% polysorbate 80 | 20% PLGA-PEG-PLGA (1500-1500-1500, LA:GA 50:50) |
| NB-0032-016-07 | 7.5 | 9% PEG400 + 8% polysorbate 80 | 17% PLGA-PEG-PLGA (1500-1500-1500, LA:GA 50:50) |
| NB-0032-017-03 | 20 | none | 16% PLGA-PEG-PLGA (1500-1500-1500, LA:GA 50:50) |
| NB-0032-017-04 | 20 | 10.5% PEG400 | |
| NB-0032-017-05 | 20 | 10.5% PEG400 + 10% polysorbate 80 | |
| NB-0032-019-04 | 10 | 10.5% PEG400 | 16 PLGA-PEG-PLGA (1500-1500-1500, LA:GA 50:50) |
| NB-0032-019-05 | | 10.5% PEG400 + 10% polysorbate 80 | |
| NB-0032-019-06 | 7.5 | 10.5% PEG400 | |
| NB-0032-019-07 | | 10.5% PEG400 + 10% polysorbate 80 | |

TABLE 1-continued

Master table of all novel gel formulations prepared using Funapide

| Lot # | Target Drug Load (mg/mL) | Solvent system | Polymer system |
|---|---|---|---|
| NB-0032-019-08 | 4 | none | |
| NB-0032-019-13 | 10 | 10.5% PEG400 + 8.5% | 17% PLGA-PEG-PLGA (1500-1500-1500, LA:GA 50:50) |
| NB-0032-019-14 | 7.5 | polysorbate 80 | |
| NB-0032-019-15 | 13 | | |
| NB-0032-019-16 | 3.5 | | |
| NB-0032-019-17 | 13 | 10.5% PEG400 | |
| NB-0032-019-18 | 3.5 | | |
| NB-0032-021-01 | 7.8 | 10% PEG400 | 16% PLGA-PEG-PLGA (1500-1500-1500, LA:GA 50:50) |
| NB-0032-021-02 | 2.6 | | |
| NB-0032-026-02 | 10 | 10.5% PEG | 16% PLGA-PEG-PLGA (1500-1500-1500, LA:GA 50:50) |
| NB-0032-027-01 | 10 | 10.5% PEG | 10% PLGA-PEG-PLGA (1100-1100-1100, LA:GA 75:25) |
| NB-0032-027-02 | | | 12% PLGA-PEG-PLGA (1100-1100-1100, LA:GA 75:25) |
| NB-0032-027-03 | | | 14% PLGA-PEG-PLGA (1100-1100-1100, LA:GA 75:25) |
| NB-0032-027-04 | | 10.5% PEG + 9% | 10% PLGA-PEG-PLGA (1100-1100-1100, LA:GA 75:25) |
| NB-0032-027-05 | | polysorbate 80 | 12% PLGA-PEG-PLGA (1100-1100-1100, LA:GA 75:25) |
| NB-0032-027-06 | | | 14% PLGA-PEG-PLGA (1100-1100-1100, LA:GA 75:25) |
| NB-0032-027-07 | | 10.5% PEG | 10% PLGA-PEG-PLGA (1600-1000-1600, LA:GA 50:50) |
| NB-0032-027-08 | | | 12% PLGA-PEG-PLGA (1600-1000-1600, LA:GA 50:50) |
| NB-0032-027-09 | | | 14% PLGA-PEG-PLGA (1600-1000-1600, LA:GA 50:50) |
| NB-0032-027-10 | | 10.5% PEG + 9% | 10% PLGA-PEG-PLGA (1600-1000-1600, LA:GA 50:50) |
| NB-0032-027-11 | | polysorbate 80 | 12% PLGA-PEG-PLGA (1600-1000-1600, LA:GA 50:50) |
| NB-0032-027-12 | | | 14% PLGA-PEG-PLGA (1600-1000-1600, LA:GA 50:50) |
| NB-0032-027-13 | | 10.5% PEG | 9% PLGA-PEG-PLGA (1100-1100-1100, LA:GA 75:25) + 3% PLGA-PEG-PLGA (1500-1500-1500, LA:GA 50:50) |
| NB-0032-027-14 | | | 10.5% PLGA-PEG-PLGA (1100-1100-1100, LA:GA 75:25) + 3.5% PLGA-PEG-PLGA (1500-1500-1500, LA:GA 50:50) |
| NB-0032-027-15 | | | 6% PLGA-PEG-PLGA (1100-1100-1100, LA:GA 75:25) + 6% PLGA-PEG-PLGA (1500-1500-1500, LA:GA 50:50) |
| NB-0032-027-16 | | | 7% PLGA-PEG-PLGA (1100-1100-1100, LA:GA 75:25) + 7% PLGA-PEG-PLGA (1500-1500-1500, LA:GA 50:50) |
| NB-0032-027-21 | 5 | 10.5% PEG | 12% PLGA-PEG-PLGA (1100-1100-1100, LA:GA 75:25) |
| NB-0032-027-22 | | | 12% PLGA-PEG-PLGA (1600-1000-1600, LA:GA 50:50) |
| NB-0032-027-23 | | | 9% PLGA-PEG-PLGA (1100-1100-1100, LA:GA 75:25) + 3% PLGA-PEG-PLGA (1500-1500-1500, LA:GA 50:50) |
| NB-0032-027-24 | | | 6% PLGA-PEG-PLGA (1100-1100-1100, LA:GA 75:25) + 6% PLGA-PEG-PLGA (1500-1500-1500, LA:GA 50:50) |
| NB-0032-027-26 | 10 | 11% PEG | 6% PLGA-PEG-PLGA (1100-1100-1100, LA:GA 75:25) |
| NB-0032-027-27 | | 10% PEG + 5% polysorbate 80 | 6% PLGA-PEG-PLGA (1500-1500-1500, LA:GA 50:50) |
| NB-0032-027-28 | | 10% PEG + 9% polysorbate 80 | |
| NB-0032-027-29 | | 11% PEG | 7% PLGA-PEG-PLGA (1100-1100-1100, LA:GA 75:25) + |
| NB-0032-027-30 | | 10% PEG + 5% polysorbate 80 | 7% PLGA-PEG-PLGA (1500-1500-1500, LA:GA 50:50) |
| NB-0032-027-31 | | 10% PEG + 9% polysorbate 80 | |
| NB-0032-027-32 | | 11% PEG | 7% PLGA-PEG-PLGA (1600-1000-1600, LA:GA 50:50) + |
| NB-0032-027-33 | | 10% PEG + 5% polysorbate 80 | 7% PLGA-PEG-PLGA (1500-1500-1500, LA:GA 50:50) |
| NB-0032-027-34 | | 10% PEG + 9% polysorbate 80 | |
| NB-0032-027-35 | | 10% PEG + 5% polysorbate 80 | 19% PLGA-PEG-PLGA (1500-1500-1500, LA:GA 50:50) |
| NB-0032-027-36 | | 10% PEG + 9% polysorbate 80 | |
| NB-0032-027-37 | | 10% PEG + 5% polysorbate 80 | |
| NB-0032-027-38 | | 10% PEG + 9% polysorbate 80 | 18% PLGA-PEG-PLGA (1500-1500-1500, LA:GA 50:50) |
| NB-0032-027-39 | 7.5 | | |
| NB-0032-027-40 | 5 | | |
| NB-0032-027-41 | 10 | 11% PEG | 9% PLGA-PEG-PLGA (1100-1100-1100, LA:GA 75:25) + 3% PLGA-PEG-PLGA (1500-1500-1500, LA:GA 50:50) |
| NB-0032-027-42 | 10 | 11% PEG | 4.5% PLGA-PEG-PLGA (1100-1100-1100, LA:GA 75:25) + |
| NB-0032-027-43 | 23 | | 4.5% PLGA-PEG-PLGA (1500-1500-1500, LA:GA 50:50) |
| NB-0032-027-44 | 13 | 11% PEG + 2% DMA | |
| NB-0032-027-45 | 12.5 | 11% PEG + 5% polysorbate 80 | |
| NB-0032-027-46 | 25.5 | 11% PEG + 5% polysorbate 80 + 2% DMA | |
| NB-0032-027-47 | 10 | 11% PEG | 6% PLGA-PEG-PLGA (1100-1100-1100, LA:GA 75:25) + |
| NB-0032-027-48 | 23 | 11% PEG + 2% DMA | 6% PLGA-PEG-PLGA (1500-1500-1500, LA:GA 50:50) |
| NB-0032-027-49 | 13 | | |

TABLE 1-continued

Master table of all novel gel formulations prepared using Funapide

| Lot # | Target Drug Load (mg/mL) | Solvent system | Polymer system |
|---|---|---|---|
| NB-0032-027-50 | 12.5 | 11% PEG + 5% polysorbate 80 | |
| NB-0032-027-51 | 25.5 | 11% PEG + 5% polysorbate 80 + 2% DMA | |
| NB-0032-027-52 | 10 | 11% PEG | 15% PLGA-PEG-PLGA (1500-1500-1500, LA:GA 50:50) |
| NB-0032-027-53 | 23 | 11% PEG + 2% DMA | |
| NB-0032-027-54 | 13 | | |
| NB-0032-027-55 | 12.5 | 11% PEG + 5% polysorbate 80 | |
| NB-0032-027-56 | 25.5 | 11% PEG + 5% polysorbate 80 + 2% DMA | |
| NB-0032-027-57 | 10 | 11% PEG | 7.5% PLGA-PEG-PLGA (1100-1100-1100, LA:GA 75:25) + 2.5% PLGA-PEG-PLGA (1500-1500-1500, LA:GA 50:50) |
| NB-0032-027-58 | 12.5 | 11% PEG + 5% polysorbate 80 | |
| NB-0032-027-59 | 13 | 11% PEG + 5% polysorbate 80 + 2% DMA | |
| NB-0032-027-60 | 18 | 11% PEG + 5% polysorbate 80 + 2% DMA | 15% PLGA-PEG-PLGA (1500-1500-1500, LA:GA 50:50) |
| NB-0032-027-61 | 10 | 10.5% PEG | 18% PLGA-PEG-PLGA (1500-1500-1500, LA:GA 50:50) |
| NB-0032-027-62 | 15 | 10.5% PEG + 5% polysorbate 80 | |
| NB-0032-027-63 | | 10.5% PEG + 2% DMA | |
| NB-0032-027-64 | | 10.5% PEG + 5% polysorbate 80 + 2% DMA | |
| NB-0032-027-65 | 10 | 10.5% PEG | 22% PLGA-PEG-PLGA (1500-1500-1500, LA:GA 50:50) |
| NB-0032-027-66 | 15 | 10.5% PEG + 5% polysorbate 80 | |
| NB-0032-027-67 | | 10.5% PEG + 2% DMA | |
| NB-0032-027-68 | | 10.5% PEG + 5% polysorbate 80 + 2% DMA | |
| NB-0032-027-69 | 10 | 10.5% PEG + 2% DMA | 6% PLGA-PEG-PLGA (1100-1100-1100, LA:GA 75:25) + 6% PLGA-PEG-PLGA (1500-1500-1500, LA:GA 50:50) |
| NB-0032-027-70 | 15 | | |
| NB-0032-027-71 | 9 | 10.5% PEG | 15% PLGA-PEG-PLGA (1500-1500-1500, LA:GA 50:50) |
| NB-0032-027-72 | 15 | 10% PEG + 2% DMA | 4.5% PLGA-PEG-PLGA (1100-1100-1100, LA:GA 75:25) + 4.5% PLGA-PEG-PLGA (1500-1500-1500, LA:GA 50:50) |
| NB-0032-31-01 | 14 | 10.5% PEG + 1.8% DMA | 19% PLGA-PEG-PLGA (1500-1500-1500, LA:GA 50:50) |
| NB-0032-31-02 | 12 | 10.4% PEG + 1.7% DMA | 15% PLGA-PEG-PLGA (1500-1500-1500, LA:GA 50:50) |
| NB-0032-031-03 | 13 | 10.5% PEG +1.8% DMA | 6% PLGA-PEG-PLGA (1100-1100-1100, LA:GA 75:25) + 6% PLGA-PEG-PLGA (1500-1500-1500, LA:GA 50:50) |
| NB-0032- 31-04 | 9 | 10.6% PEG | 15% PLGA-PEG-PLGA (1500-1500-1500, LA:GA 50:50) |
| NB-0032-039-07 | 10 | 10% PEG + 1.8% DMA | 16% PLGA-PEG-PLGA (1400-1500-1400, LA:GA 50:50) |
| NB-0032-032-03 | 15 | 11% PEG 400 + 1.8% DMA | 19% PLGA-PEG-PLGA (1500-1500-1500, LA:GA 50:50) |
| NB-0032-040-01 | 13 | 10.5% PEG + 1.8% DMA | 16% PLGA-PEG-PLGA (1400-1500-1400, LA:GA 50:50) |
| NB-0032-040-02 | 13 | | 18% PLGA-PEG-PLGA (1400-1500-1400, LA:GA 50:50) |
| NB-0032-040-03 | 13 | | 19% PLGA-PEG-PLGA (1400-1500-1400, LA:GA 50:50) |
| NB-0032-040-04 | 13 | | |
| NB-0032-040-05 | 15 | 10.5% PEG + 1.8% DMA | 21% PLGA-PEG-PLGA (1400-1500-1400, LA:GA 50:50) |
| NB-0032-040-06 | 17 | | |
| NB-0032-040-07 | 13 | | 22% PLGA-PEG-PLGA (1400-1500-1400, LA:GA 50:50) |
| NB-0032-040-08 | 15 | | |

Figure 2:
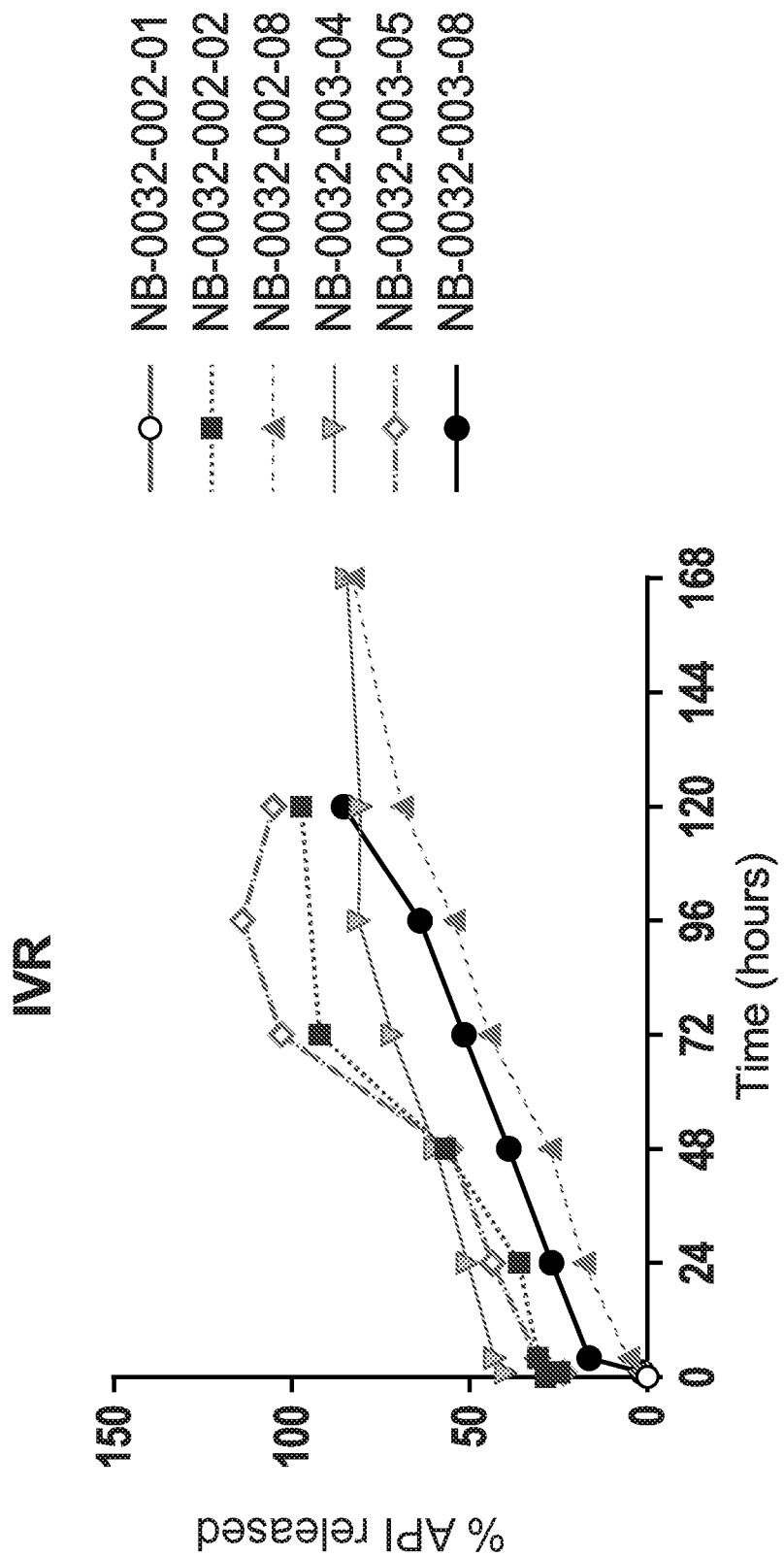
FIG. 2 In vitro release profile of initial formulations.
Figure 3:
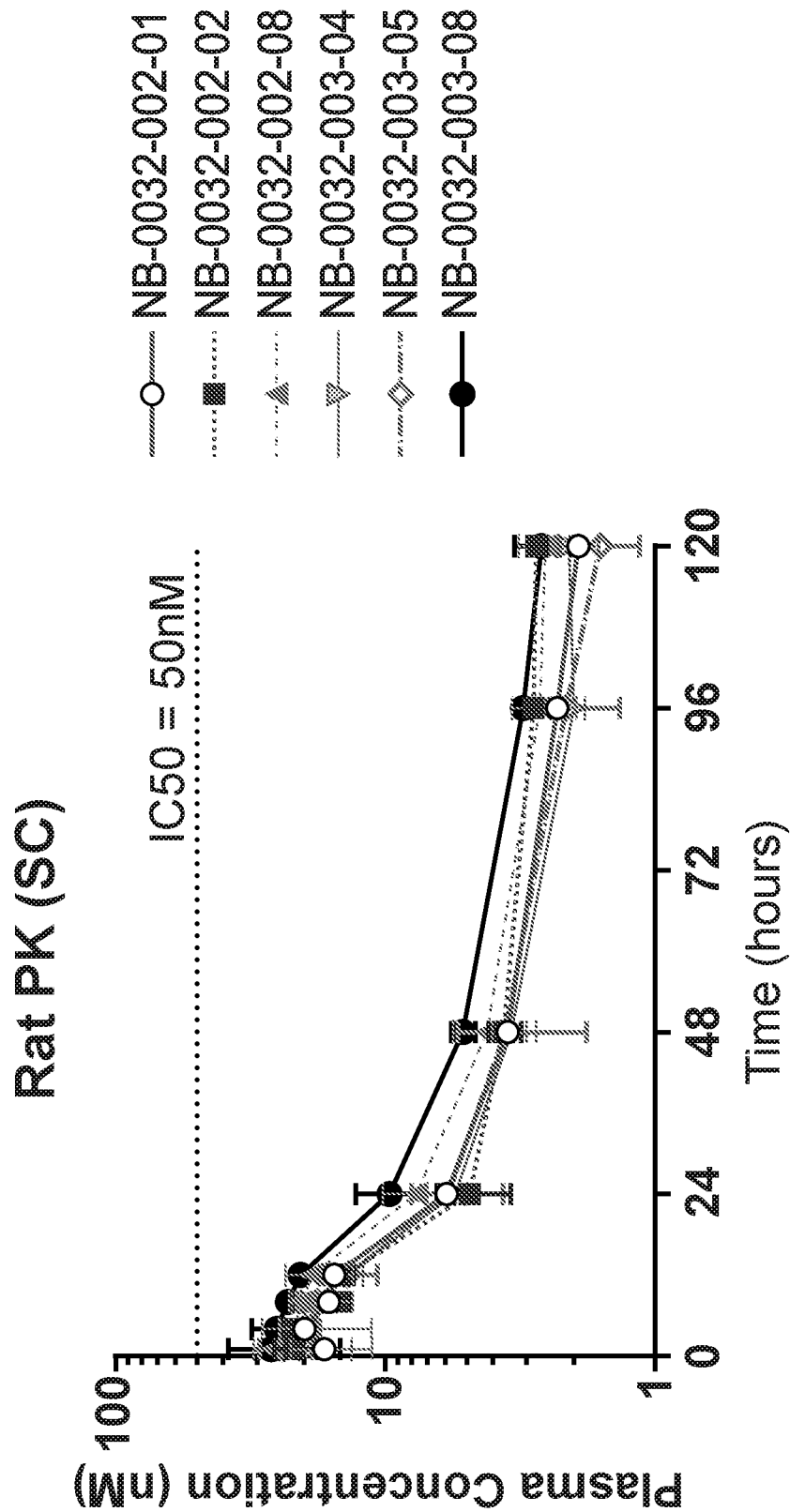
FIG. 3. Rat PK study performed using the initial formulations.

Initial formulation efforts focused on using triblock PLGA-PEG-PLGA polymer in the molecular weight range of ~6 kDa. Due to high molecular weight of the polymer, some of these polymers were only soluble up to 12-15%. The formulations made with these polymers (as summarized in Table 2) lead to insufficient drug loading. Secondly, the drug release from these formulations as characterized using an in vitro release assay (shown in FIG. 2) was fast and the in vivo drug exposure (FIG. 3) obtained from the formulations was low and short lived as well.

TABLE 2

Summary of initial scouting formulations

| Lot# | Target Drug Load (mg/mL) | Measured Drug Load (mg/mL) | Solvent System (w/w) | Polymer system (w/w) |
|---|---|---|---|---|
| NB-0032-002-01 | 5 | 3.7 | 2.5% DMA + 9.4% polysorbate 80 | 10.6% PLGA-PEG-PLGA (2200-1500-2200, LA:GA 50:50) |
| NB-0032-002-02 | 5 | 3.2 | 2.4% DMA + 9.1% polysorbate 80 | 12.9% PLGA-PEG-PLGA (2200-1500-2200, LA:GA 50:50) |
| NB-0032-002-08 | 5 | 4.5 | 2.3% DMA + 8.8% polysorbate 80 | 12.4% PLGA-PEG-PLGA (1500-1500-1500, LA:GA 50:50) + 4.1% PLGA-PEG-PLGA (1600-1000-1600, LA:GA 50:50) (16.5% total polymer) |
| NB-0032-003-04 | 5 | 4.2 | 6.5% PEG400 + 9.1% polysorbate 80 | 12.8% PLGA-PEG-PLGA (1700-1500-1700, LA:GA 75:25) |
| NB-0032-003-05 | 5 | 3.2 | 6.4% PEG400 + 8.9% polysorbate 80 | 14.3% PLGA-PEG-PLGA (1700-1500-1700, LA:GA 75:25) |
| NB-0032-003-08 | 5 | 3.8 | 6.2% PEG400 + 8.7% polysorbate 80 | 8.2% PLGA-PEG-PLGA (1500-1500-1500, LA:GA 50:50) + 8.2% PLGA-PEG-PLGA (1600-1000-1600, LA:GA 50:50) (16.4% total polymer) |

Figure 4:
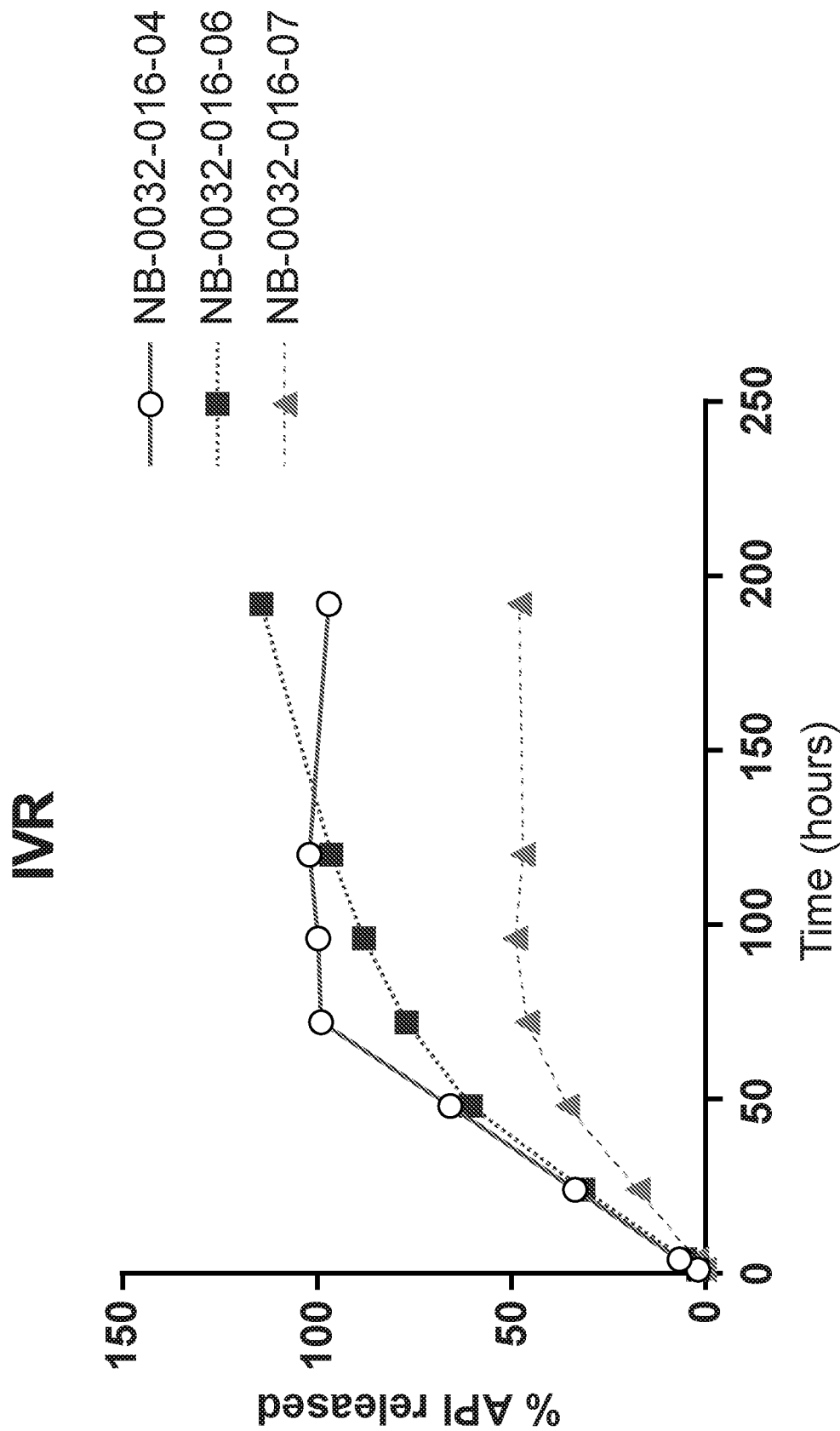
FIG. 4. In vitro release profile of formulations containing higher polymer concentration.
Figure 5:
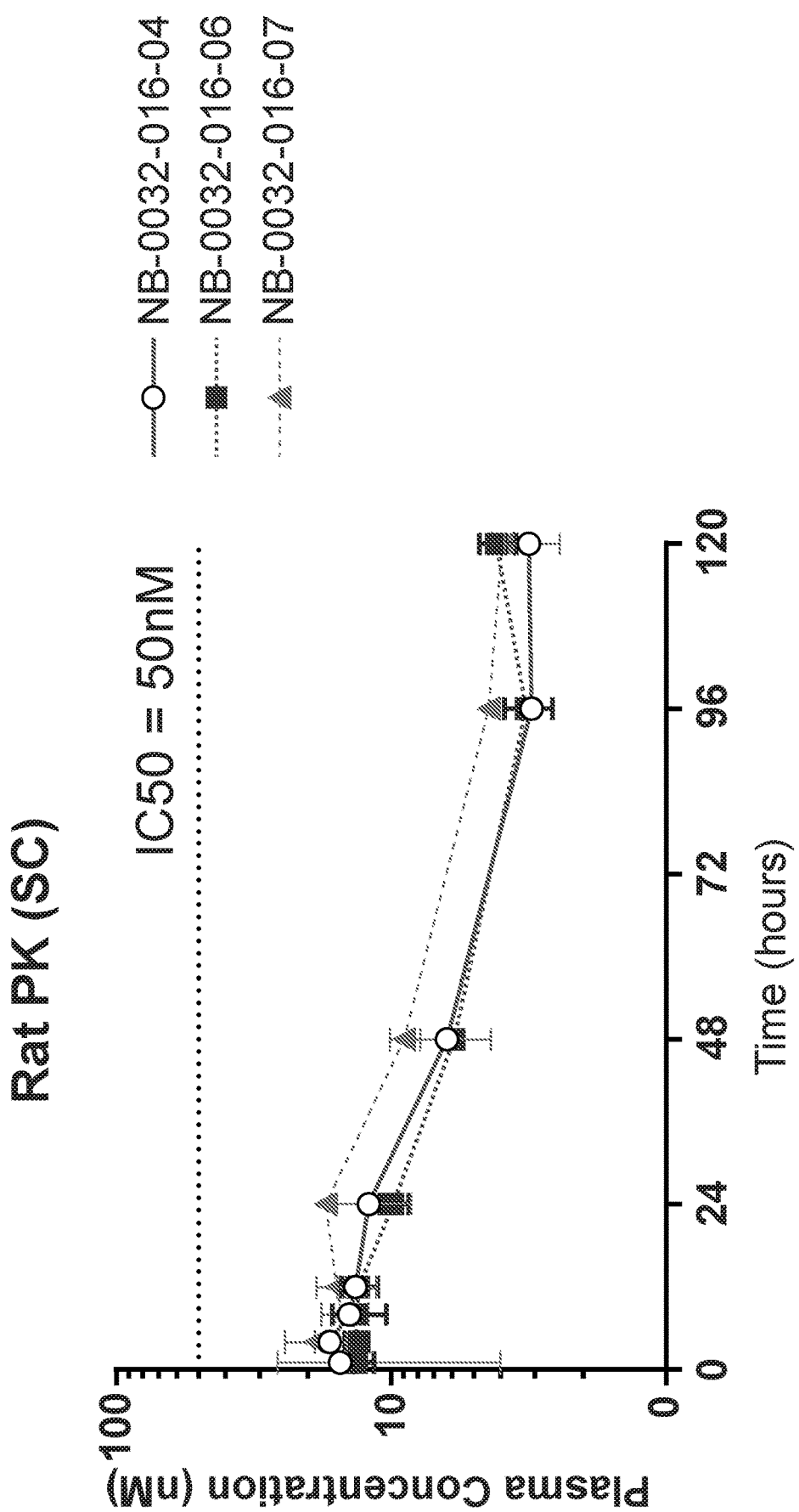
FIG. 5 Rat PK study performed using formulations containing higher polymer concentration.

The results from in vitro and in vivo data from the initial formulations, disclosed herein suggested that increasing the drug load was essential for achieving higher doses for in vivo studies. The polymer concentration in the formulation was increased to achieve higher drug encapsulation. Slightly less hydrophobic polymers (such as PLGA-PEG-PLGA (1500-1500-1500, LA:GA 50:50), refer to Table 3 for polymer composition and MW details) were able to be dissolved at 16% to 20%. Since such high polymer concentrations were achieved with PLGA-PEG-PLGA (1500-1500-1500, LA:GA 50:50), PLGA-PEG-PLGA (1500-1500-1500, LA:GA 50:50) was selected as the lead polymer. In order to further increase the solubility of the API within the formulation, the PEG 400 percentage was also increased to about 10%. As seen in Table 3, the use of higher polymer concentration and higher PEG 400 resulted in higher drug loads within the formulation. However, the in vitro release profiles (FIG. 4) were still sub-optimal and the in vivo drug exposures (FIG. 5) were still well below the $IC_{50}$ concentration even with these formulations.

TABLE 3

Increased polymer concentration led to higher drug load

| Lot# | Target Drug Load (mg/mL) | Measured Drug Load (mg/mL) | Solvent System (w/w) | Polymer system (w/w) |
|---|---|---|---|---|
| NB-0032-016-04 | 5 | 3.7 | 6.2% PEG 400 + 8.7% polysorbate 80 | 16.4% PLGA-PEG-PLGA (1500-1500-1500, LA:GA 50:50) |
| NB-0032-016-06 | 5 | 3.2 | 6.0% PEG 400 + 8.3% polysorbate 80 | 19.7% PLGA-PEG-PLGA (1500-1500-1500, LA:GA 50:50) |
| NB-0032-016-07 | 7.5 | 5.4 | 9.2% PEG 400 + 8.6% polysorbate 80 | 16.8% PLGA-PEG-PLGA (1500-1500-1500, LA:GA 50:50) |

Figure 6:
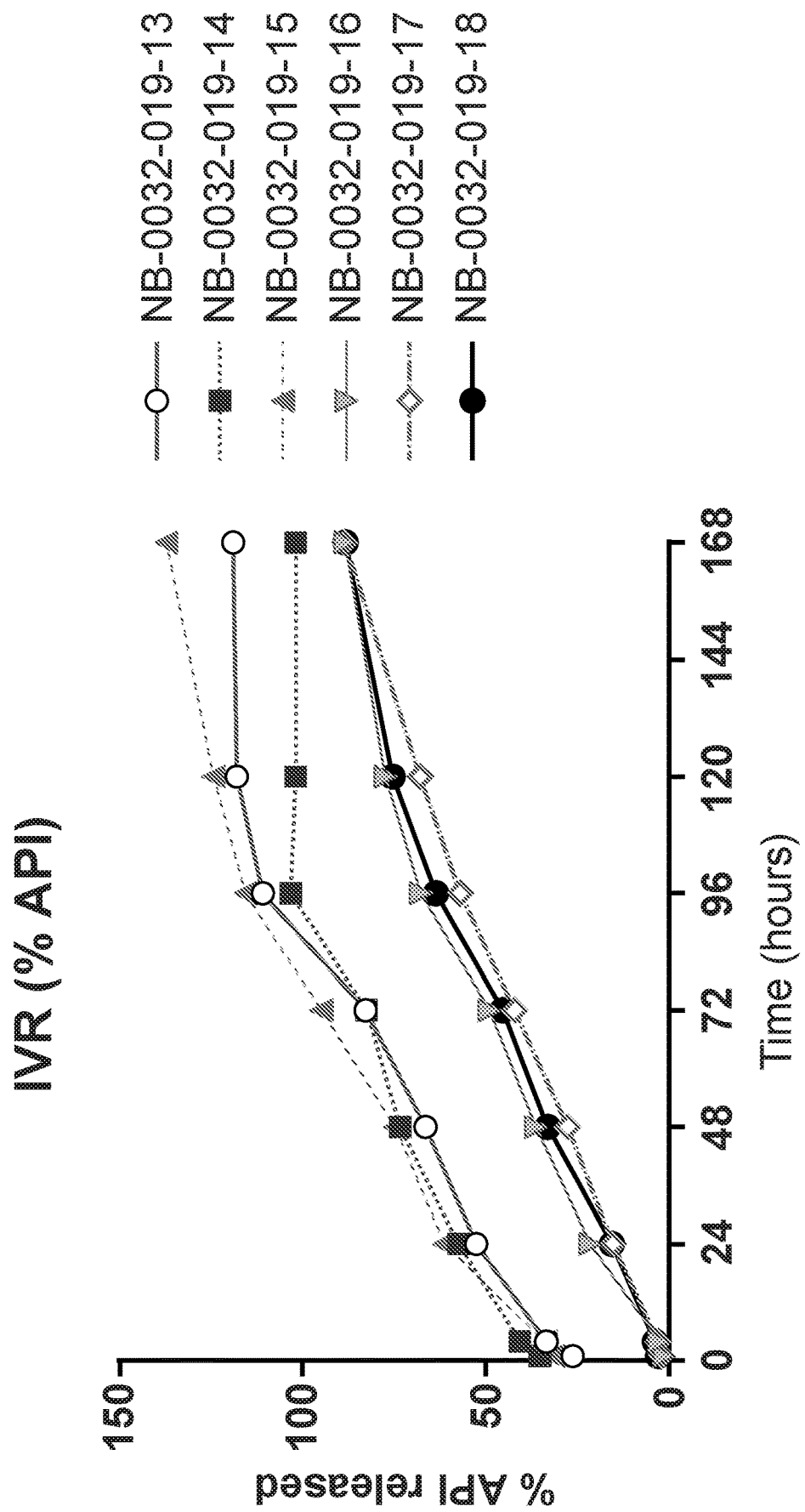
FIG. 6. Comparing in vitro release (% API release) profile of formulations with and without polysorbate 80.
Figure 7:
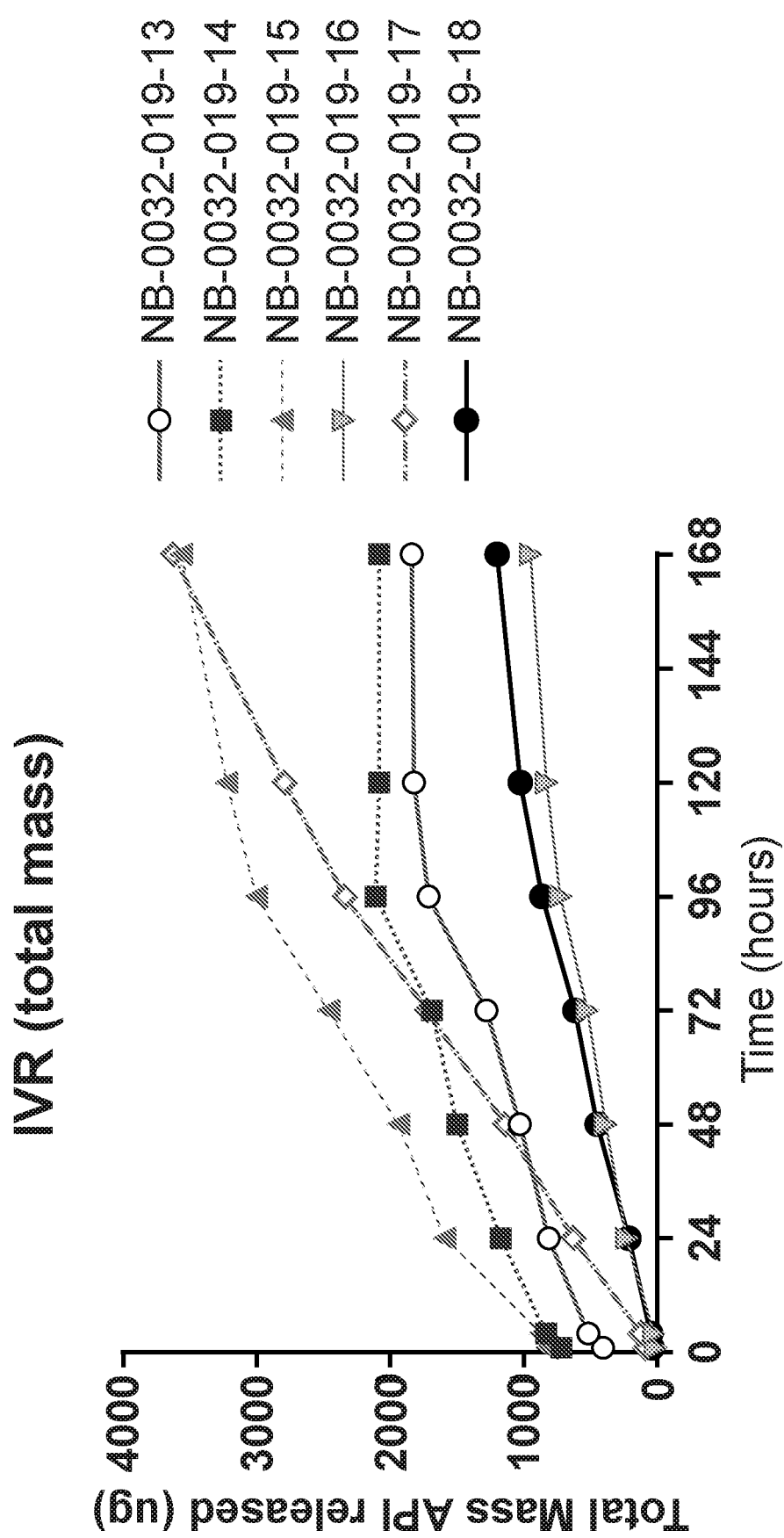
FIG. 7. Comparing in vitro release (mass released) profile of formulations with and without polysorbate 80.
Figure 8:
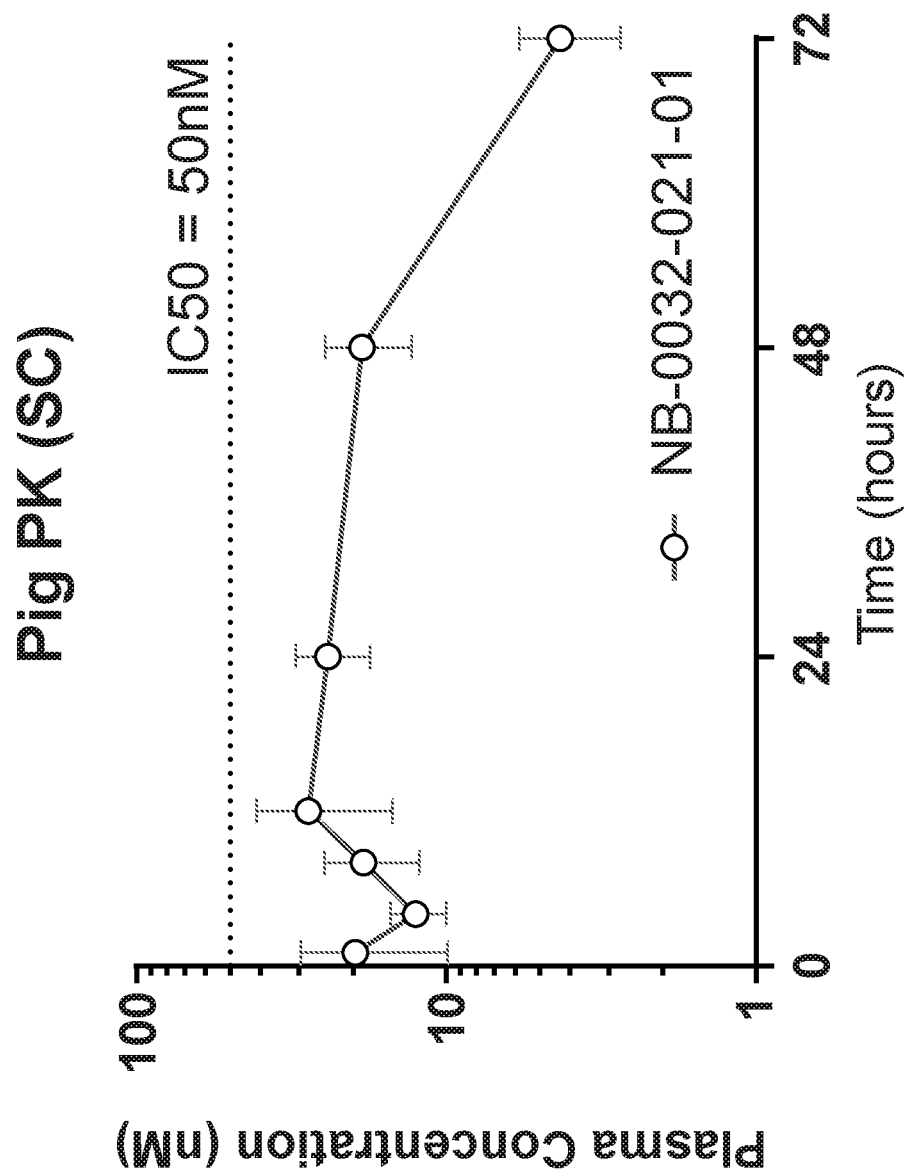
FIG. 8. Pig PK study performed using NB0032-021-01 (9.6% PEG 400+16.4% PLGA-PEG-PLGA (1500-1500-1500, LA:GA 50:50)).
Figure 9:
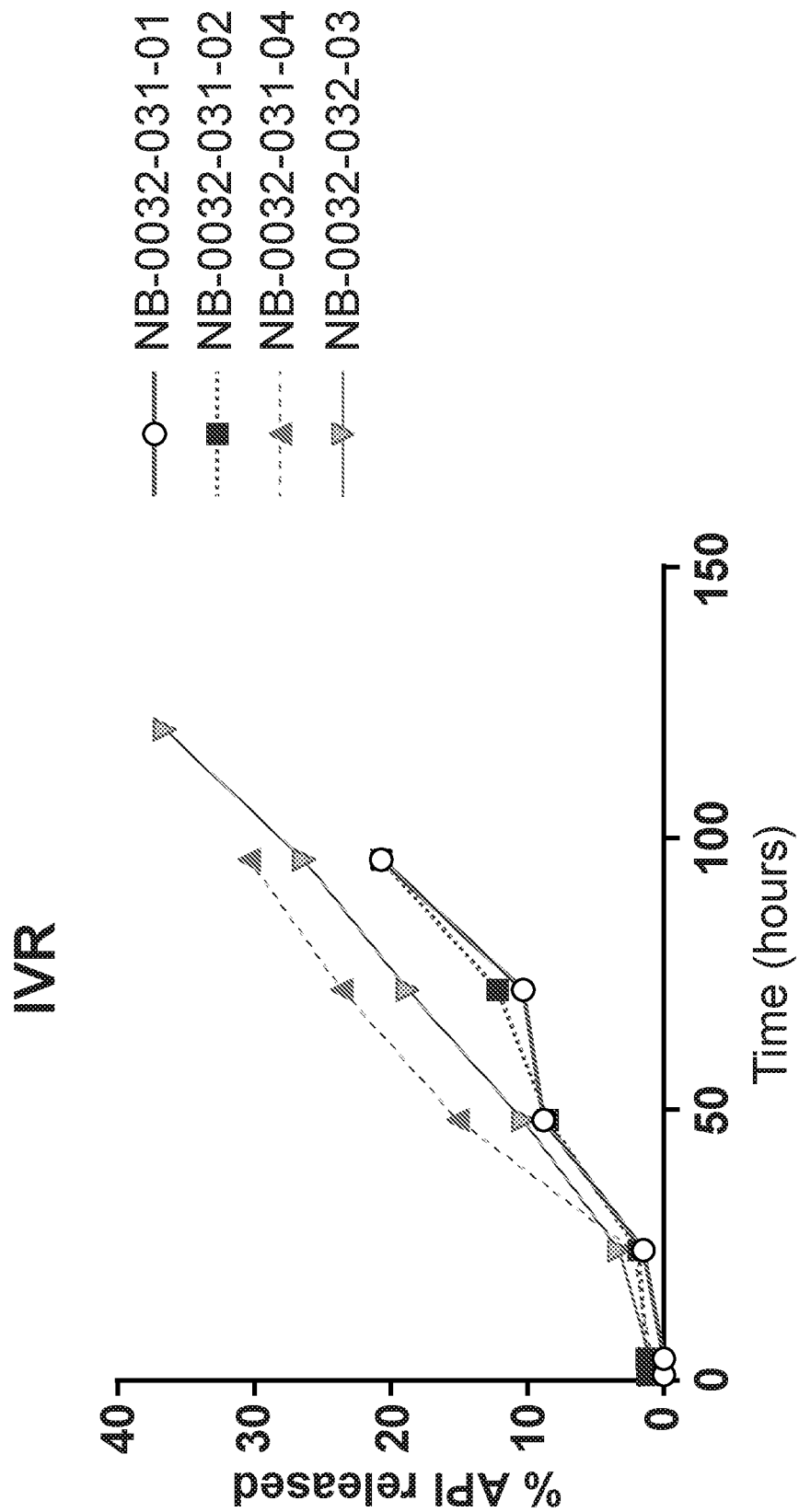
FIG. 9. Comparing in vitro release (% API released) profile of formulations with and without DMA.
Figure 10:
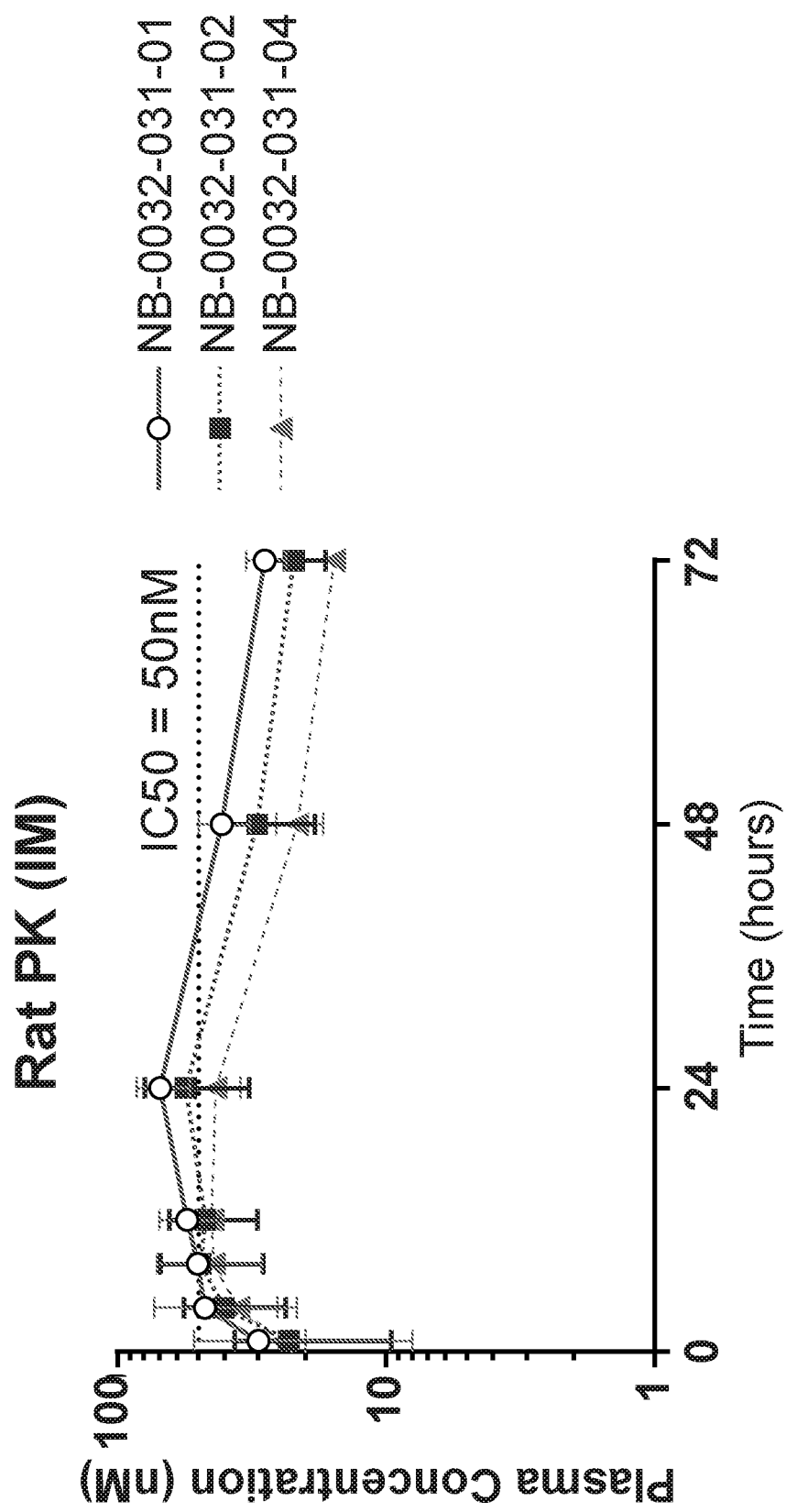
FIG. 10. Rat PK study on formulations with and without DMA.
Figure 11:
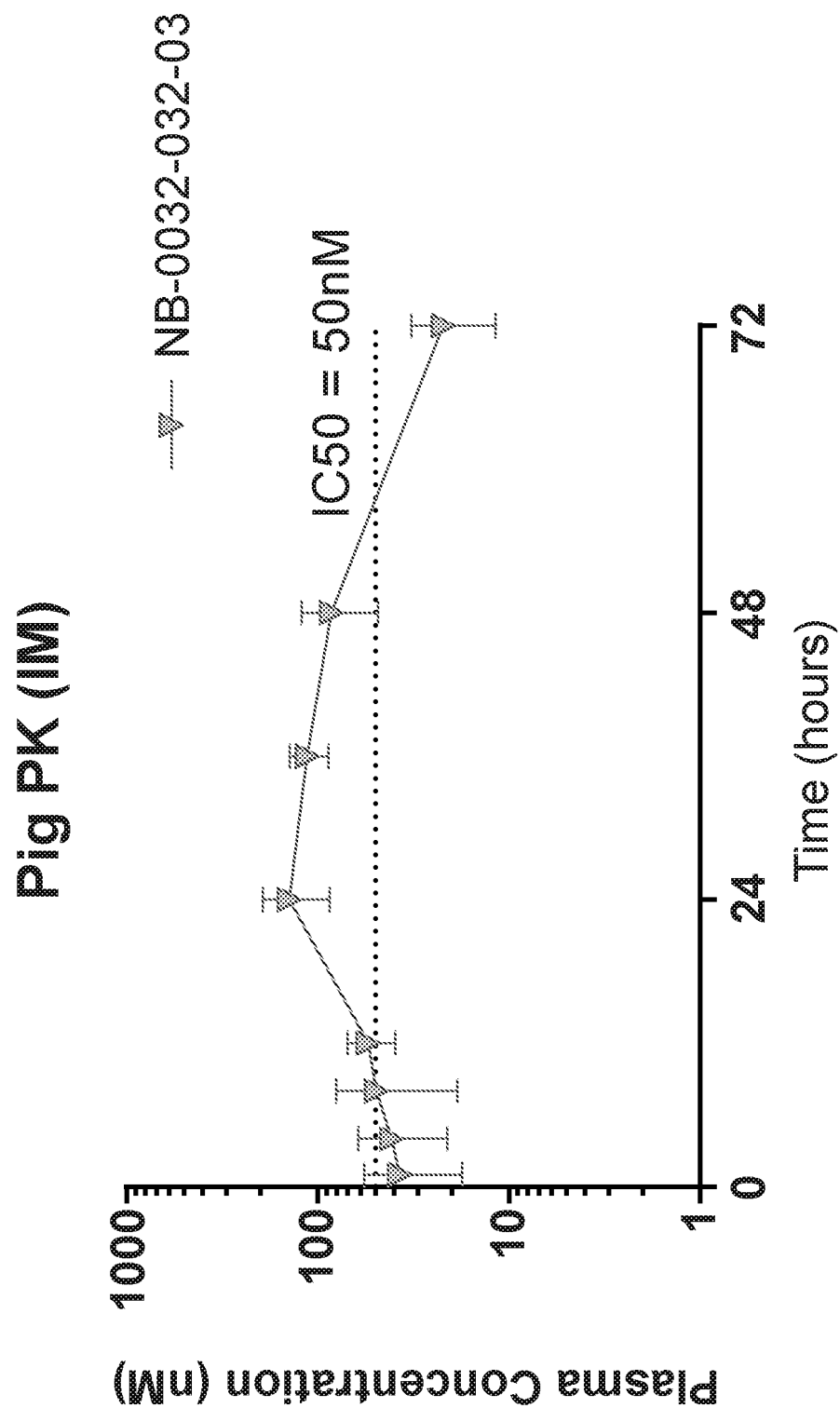
FIG. 11. Systemic PK profile of funapide-triblock polymer formulation (FX301) in Pig.

In order to further slow the release of drug, polysorbate 80 was removed from the formulation. Since polysorbate 80 is a surfactant and a hydrophilic molecule, it may interfere with the gelation process of the formulation thus potentially causing faster drug release. The formulations prepared with and without polysorbate 80 are summarized in Table 4. The results of the in vitro release data disclosed herein indicate that the formulations without polysorbate 80 showed much slower in vitro release profile (FIGS. 6 and 7) than those containing polysorbate 80. While the in vivo exposure of the API from the formulation without polysorbate 80 displayed consistent drug exposure for 3 days, the systemic levels of API were still below $IC_{50}$ concentrations (50 nM) (FIG. 8).

experimentally identified as a good drug solubilizer for this API. By adding 1.7% of DMA to the formulation, the drug load was increased to ~1.5% drug load. Drug loading information on the formulations made with 1.7% DMA and 10.5% PEG 400 are shown in Table 6. The results described herein show that while the addition of DMA increased the drug load, it did not affect the in vitro release of the formulations (shown in FIG. 9). These formulations were evaluated for in vivo exposure in a rat PK model (shown in FIG. 10) and pig PK model (shown in FIG. 11). The results

TABLE 4

Comparing drug load in formulations with and without polysorbate 80

| Lot# | Target Drug Load (mg/mL) | Measured Drug Load (mg/mL) | Solvent System (w/w) | Polymer system |
|---|---|---|---|---|
| NB-0032-017-01 | 20 | 3.9 | — | 20% PLGA-PEG-PLGA (1500-1500-1500, LA:GA 50:50) |
| NB-0032-019-13 | 10 | 4.1 | 10.5% PEG 400 + 8.4% polysorbate 80 | 16.7% PLGA-PEG-PLGA (1500-1500-1500, LA:GA 50:50) |
| NB-0032-019-14 | 7.5 | 5.5 | 10.3% PEG 400 + 8.4% polysorbate 80 | 16.7% PLGA-PEG-PLGA (1500-1500-1500, LA:GA 50:50) |
| NB-0032-019-15 | 13 | 6.9 | 10.5% PEG 400 + 8.4% polysorbate 80 | 16.6% PLGA-PEG-PLGA (1500-1500-1500, LA:GA 50:50) |
| NB-0032-019-16 | 3.5 | 2.9 | 10.6% PEG 400 + 8.5% polysorbate 80 | 16.8% PLGA-PEG-PLGA (1500-1500-1500, LA:GA 50:50) |
| NB-0032-019-17 | 13 | 10.9 | 10.5% PEG 400 | 16.6% PLGA-PEG-PLGA (1500-1500-1500, LA:GA 50:50) |
| NB-0032-019-18 | 3.5 | 3.6 | 10.6% PEG 400 | 16.8% PLGA-PEG-PLGA (1500-1500-1500, LA:GA 50:50) |

TABLE 5

Summary of formulations evaluated in Pig PK study

| Lot# | Target drug Load (mg/ml) | Measured drug Load (mg/ml) | Solvent System (w/w) | Polymer system |
|---|---|---|---|---|
| NB-0032-021-01 | 9 | 7.8 | 9.6% PEG 400 | 16.3% PLGA-PEG-PLGA (1500-1500-1500, LA:GA 50:50) |
| NB-0032-021-02 | 3 | 2.6 | 9.6% PEG 400 | 16.4% PLGA-PEG-PLGA (1500-1500-1500, LA:GA 50:50) |
| NB-0032-021-03 | 0 | 0 | 9.6% PEG 400 | 16.4% PLGA-PEG-PLGA (1500-1500-1500, LA:GA 50:50) |

In order to further increase the drug exposure, the drug loading in the formulation was increased by adding 1.7% DMA (Dimethyl Acetamide) to the formulation. DMA was disclosed herein indicate that both the PK studies show significantly higher drug exposure for the formulations with higher drug loads.

TABLE 6

Comparing drug load in formulations with and without DMA

| Lot# | Target Drug Load (mg/mL) | Measured Drug Load (mg/mL) | Solvent System (w/w) | Polymer system (w/w) |
|---|---|---|---|---|
| NB-0032-031-01 | 15 | 15.1 | 10.5% PEG 400 + 1.8% DMA | 18.9% PLGA-PEG-PLGA (1500-1500-1500, LA:GA 50:50) |
| NB-0032-031-02 | 13 | 14.5 | 10.4% PEG 400 + 1.7% DMA | 15.0% PLGA-PEG-PLGA (1500-1500-1500, LA:GA 50:50) |
| NB-0032-031-04 | 10 | 10 | 10.6% PEG 400 | 15.3% PLGA-PEG-PLGA (1500-1500-1500, LA:GA 50:50) |
| NB-0032-032-03 | 15 | 12.9 | 11.0% PEG 400 + 1.8% DMA | 19.0% PLGA-PEG-PLGA (1500-1500-1500, LA:GA 50:50) |

Figure 12:
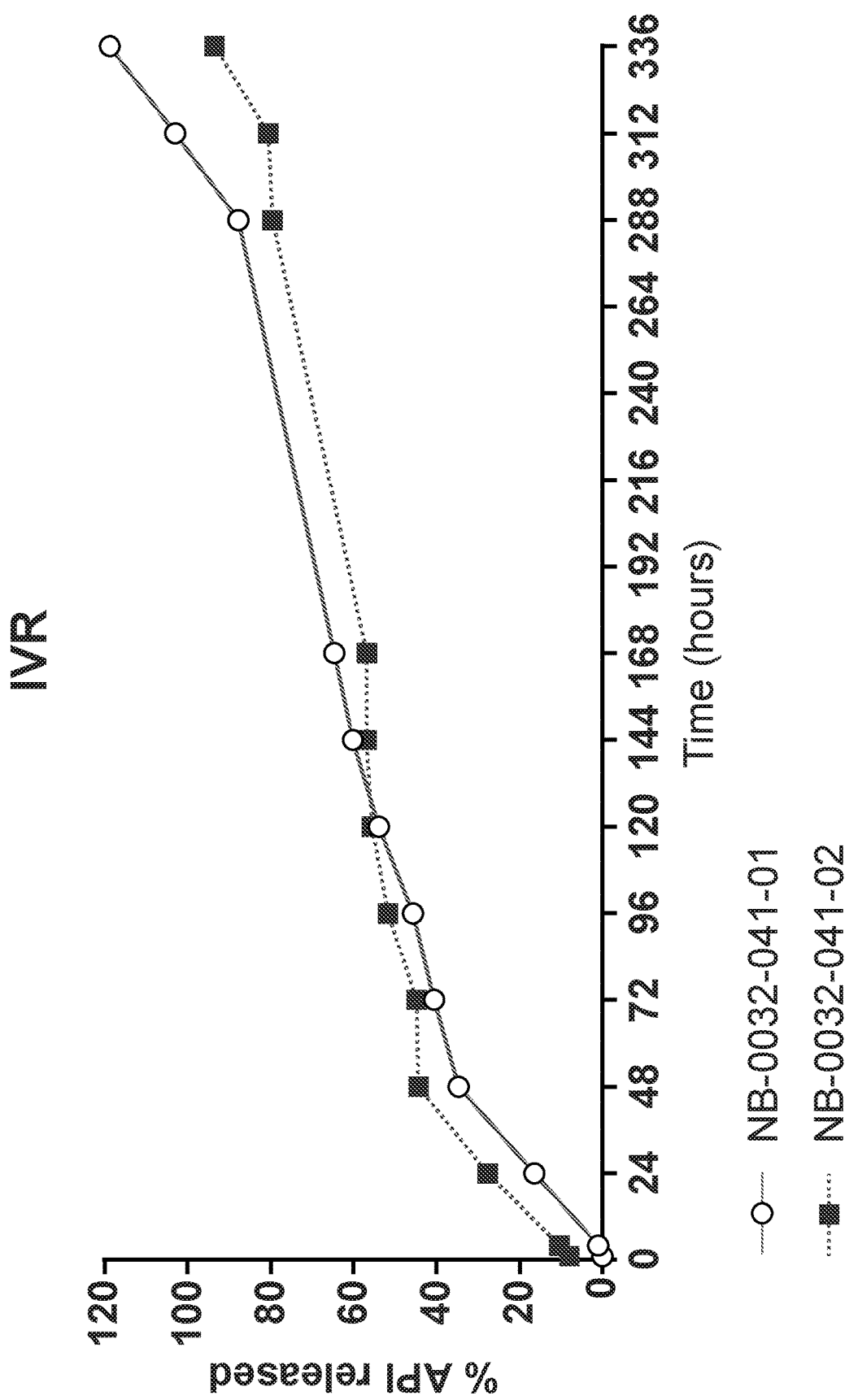
FIG. 12. In vitro release profile of the funapide-triblock polymer formulation (FX301) made with low and high MW polymer.
Figure 13:
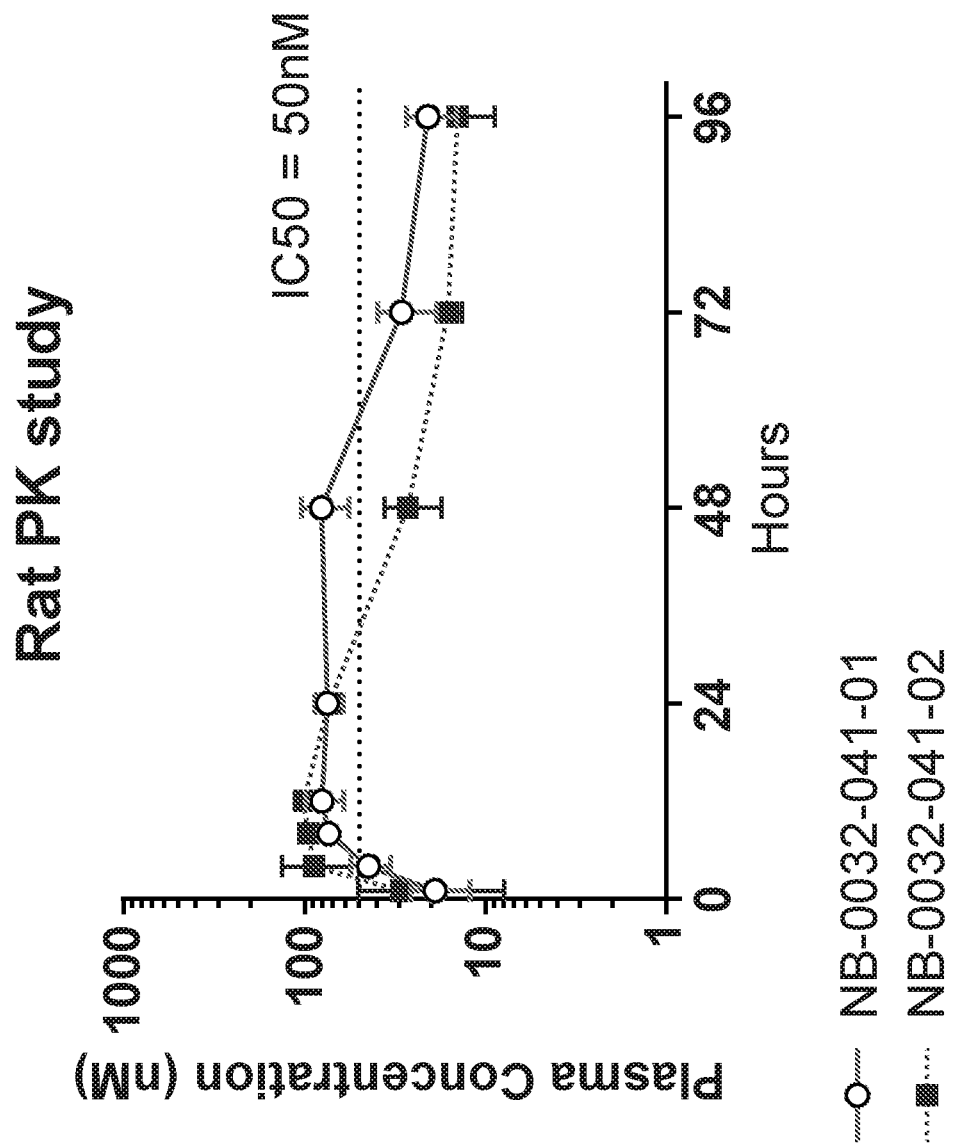
FIG. 13. Rat PK study performed using formulations prepared with low and high MW polymer.

At this point, 1.7% DMA+10.5% PEG 400+19.3% polymer was identified as the lead formulation. However, the lead polymer used in this formulation i.e. PLGA-PEG-PLGA (1500-1500-1500, LA:GA 50:50), depending on the batch of the polymer, can vary in the PLGA molecular weight. These variations mean that the actual MW may not necessarily be the exact nominal target molecular weight. Polymer batches that have slightly longer PLGA chains can have higher MW (~5400 Da) and the polymers batches with slightly shorter PLGA chains would have slightly lower MW (~3600 Da). In order to understand the impact of normal variation in polymer MW on formulation performance, formulations with high and low MW polymer were made. As seen in FIG. 12, the in vitro release profile from both MW formulations are similar. Secondly, other product attributes (shown in Table 7) such as drug load, onset of gelation and gelation temperature are comparable between the formulations. Finally, the formulations were also screened for drug exposure and duration in a rat PK study (shown in FIG. 13). The results described herein show that the selected nominal polymer, PLGA-PEG-PLGA (1500-1500-1500, LA:GA 50:50), produces consistent formulation within the MW weight range of 3600-5400 Da.

TABLE 7

Summary of formulation properties for formulations prepared with Low and High MW polymer (* the gelation properties can vary depending on the settings of the rheological measurement)

| | 19.2% high MW polymer + 10.5% PEG + 1.7% DMA | 19.2% low MW polymer + 10.5% PEG + 1.7% DMA |
|---|---|---|
| Lot Number | NB-0032-041-01 | NB-0032-041-02 |
| Polymer MW | 5423 Da | 3618 Da |
| API content (mg/mL) | 11.3 | 12.4 |
| Onset of gelation (° C.)* | 24 | 26 |
| Gelation temperature (° C.)* | 32 | 36 |
| Max G' (Pa) | 450 | 105 |
| Time to gelation (min) | ~1 min | ~2 mins |
| Time point at 100% release | 11 days | 11 days |

Figure 14:
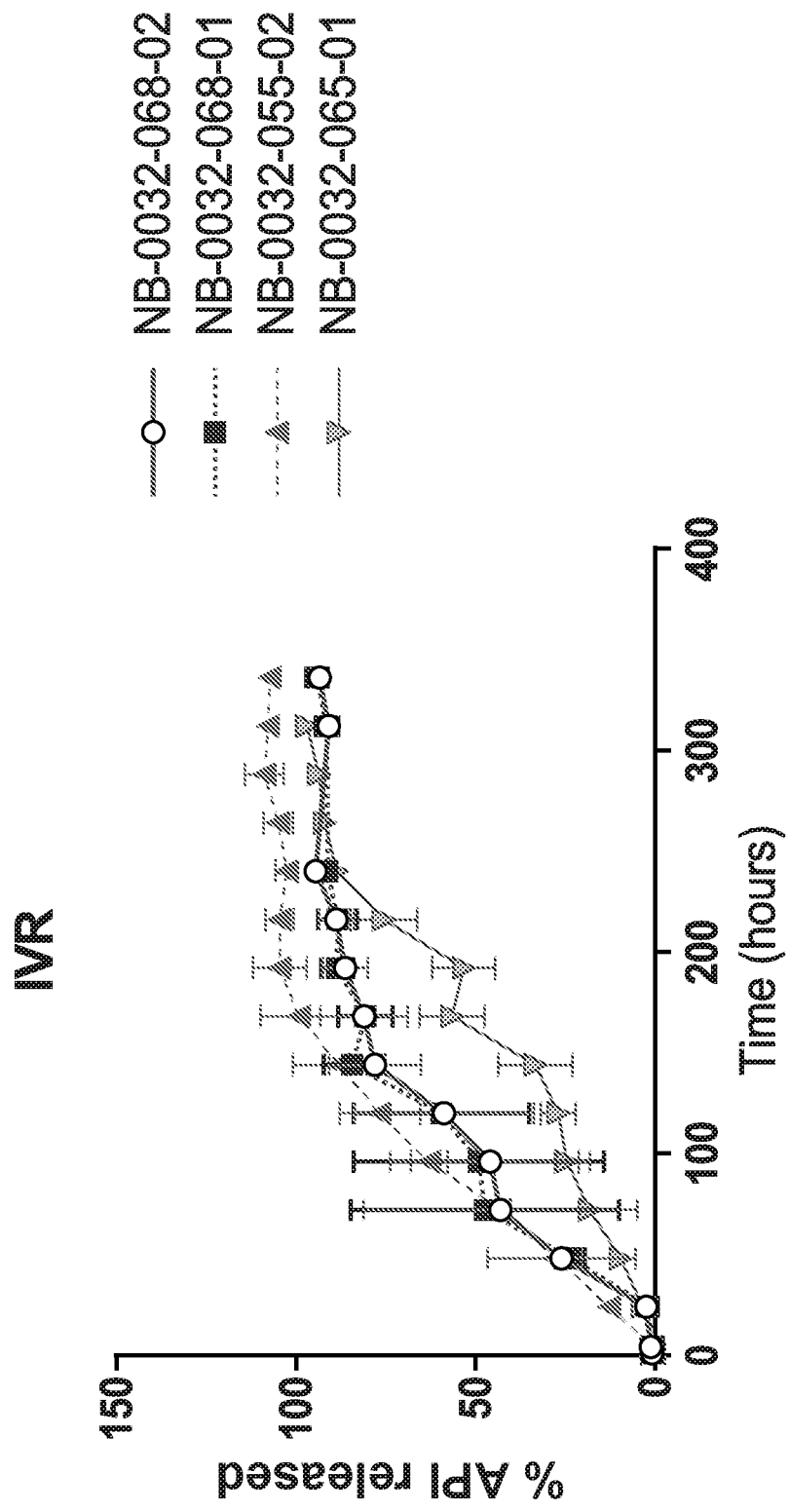
FIG. 14. In vitro release profile of the FX301 made with PLGA-PEG-PLGA polymer with MW in the range of 5600 to 6400 Da (all polymers with LA:GA 50:50).

As the polymer was scaled up, the studies described herein show there were cases of even higher MW weight polymers that were found to be suitable for FX301. The PEG block was consistent at about 1500 Da since this is established by the PEG starting material, but the PLGA side chain lengths ranged from 2050-2450 Da based on process variations in the synthetic route used to make the PLGA-PEG-PLGA triblock polymer. Polymers were prepared to cover this expanded range and formulations were prepared and evaluated. The properties of these formulations were acceptable for product performance and are detailed in Table 8. Release profiles of these formulations are provided in FIG. 14.

TABLE 8

Summary of formulation properties for formulations prepared with polymers of higher molecular weight (* the gelation properties can vary depending on the settings of the rheological measurement)

|  | 19.2% polymer PLGA-PEG-PLGA (2050-1500-2050, LA:GA 50:50) + 10.5% PEG + 1.7% DMA | 19.2% polymer PLGA-PEG-PLGA (2150-1500-2150, LA:GA 50:50 + 10.5% PEG + 1.7% DMA | 19.2% polymer PLGA-PEG-PLGA (2350-1500-2350, LA:GA 50:50) + 10.5% PEG + 1.7% DMA | 19.2% polymer PLGA-PEG-PLGA (2450-1500-2450, LA:GA 50:50) + 10.5% PEG + 1.7% DMA |
|---|---|---|---|---|
| Lot Number | NB-0032-068-02 | NB-0032-068-01 | NB-0032-055-02 | NB-0032-065-01 |
| Polymer MW | 5600 Da | 5800 Da | 6200 Da | 6400 Da |
| API content (mg/mL) | 13.9 | 14.4 | 12.8 | 12.6 |
| Onset of gelation (° C.)* | 26 | 27 | 27 | 27 |
| Gelation temperature (° C.)* | 35.9 | 35.5 | 33.4 | 35.8 |
| Max G' (Pa) | 275 | 321 | 462 | 457 |
| Time point at 100% release | 10 days | 10 days | 9 days | 12 days |

Other polymer systems were also screened during the formulation development and are listed in the Table 9.

TABLE 9

Summary of all the polymers evaluated

| Description | Polymer concentration in the formulation |
|---|---|
| PCL-PEG-PCL (Mw 1000:1000:1000) | 20% |
| PLGA-PEG-PLGA (LG 50:50) (Mw 2000:2000:2000) | 20%, 13%, 6.5% |
| PLGA-PEG-PLGA (LG 50:50) (Mn 1000:1000:1000) | 20%, 15%, 11% |
| PLGA-PEG-PLGA (LG 75:25) (Mn 1000:1000:1000) | 20%, 15%, 11% |
| PLGA-PEG-PLGA (LG 50:50) (Mw 400:3000:400) | 20% |
| PLGA-PEG-PLGA (LG 95:5) (Mn 1500:1500:1500) | 20%, 16.5% |
| PLGA-PEG-PLGA (LG 85:14) (Mw 1500:1500:1500) | 20%, 13% |
| PLGA-PEG-PLGA (LG 75:25) (Mw 1700:1500:1700) | 20%, 11% |
| PLGA-PEG-PLGA (LG 75:25) (Mn 1600:1500:1600) | 20%, 13% |
| PDLLA-PEG-PDLLA (Mn 1700:1500:1700) | 20%, 16.5%, 15% |

The results of the instant disclosure, show that the solubility of the tri-block polymer system, and the solubility and dissolution rate (during compounding) of the drug (funapide) into the polymer solution, is dependent on a combination of the following parameters: molecular weight of each polymer block of the tri-block polymer, total molecular weight of the tri-block polymer, and the relative final concentrations of the triblock polymer, drug, solvent and solubility enhancer in the composition. The study described herein shows how alteration of the specific parameters of the composition, as disclosed herein affects the polymer solubility, gelation temperatures, amount of drug load and in vitro release rate of the drug from the compositions as described herein.

Example 3: Efficacy and Pharmacokinetics of Peripheral Nerve Block by FX301, in a Postoperative Pain Model in Pigs Introduction FX301 is injected near the site of a peripheral nerve in a liquid state and forms a viscous pliable gel at body temperature that coats the exterior of the nerve to block the propagation of sensory nerve signals. Described herein is a study evaluating the efficacy and pharmacokinetic profile of FX301 delivered as a sciatic nerve block in a validated postoperative pain model in pigs.
Summary of Data Generated from Pig Study (Pigs Dosed at 13 mg/mL, 10 mL Total Dose Prior to Surgery)
Evaluation of the Efficacy and PK Profile of FX301 Delivered Via Ultrasound-Guided Sciatic Nerve Block in a Validated Postoperative Pain Model in Pigs A total of 18 young adult male pigs were assigned to 1 of 3 study groups: vehicle (n=6), FX301 (n=6), and liposomal bupivacaine (n=6). An additional 3 pigs were treated with FX301 to evaluate local and systemic exposure of funapide. Following habituation for 5 days, pigs were injected with 10 ml of vehicle, FX301 (13 mg/mL; total dose 130 mg), or liposomal bupivacaine (13.3 mg/mL; total dose 133 mg) to the proximity of the sciatic nerve under ultrasound guidance. Postoperative pain was induced by a 5 cm long surgical incision in the dorsal area of the hind leg. Pain was evaluated using both von Frey testing and General Behavior Scoring (GBS) administered at baseline, and at 1, 4, 8, 12, 24, 36, 48, and 72 hours after injection. Open field testing for locomotor activity (total walking distance in 5 min) was performed at baseline and at 2 and 24 hours after injection. Comparisons between treatment and vehicle groups were performed using one-way analysis of variance followed by Tukey test; a p value <0.05 was considered statistically significant. Plasma samples for PK analysis were collected at baseline, and at 1, 4, 8, 12, 24, 36, 48, and 72 hours after injection. Local muscle samples from the site of injection were collected at baseline and at 72 hours after injection. Funapide was quantified in plasma and muscle homogenate samples using high-performance liquid chromatography with tandem mass spectrometry detection.

Figure 15B:
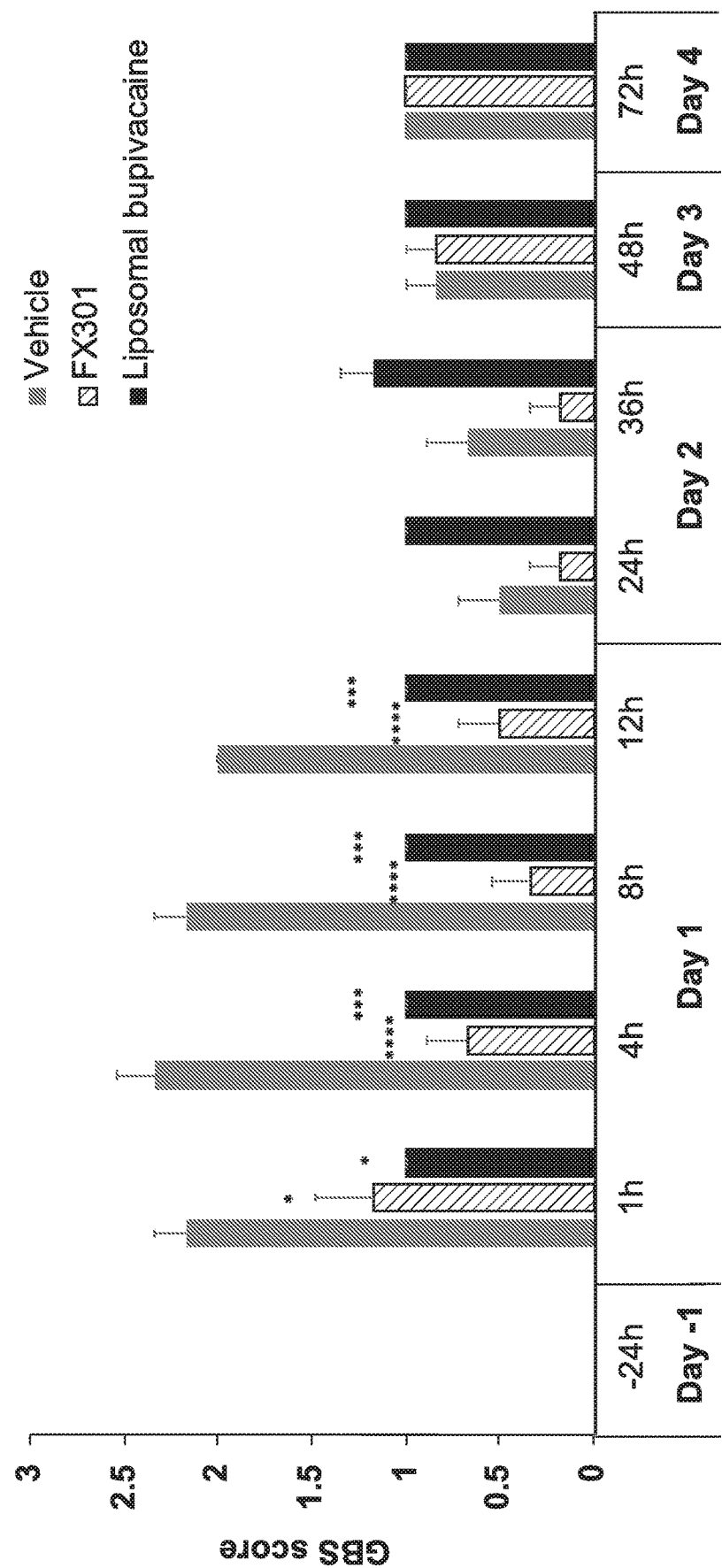
Figure 15C:
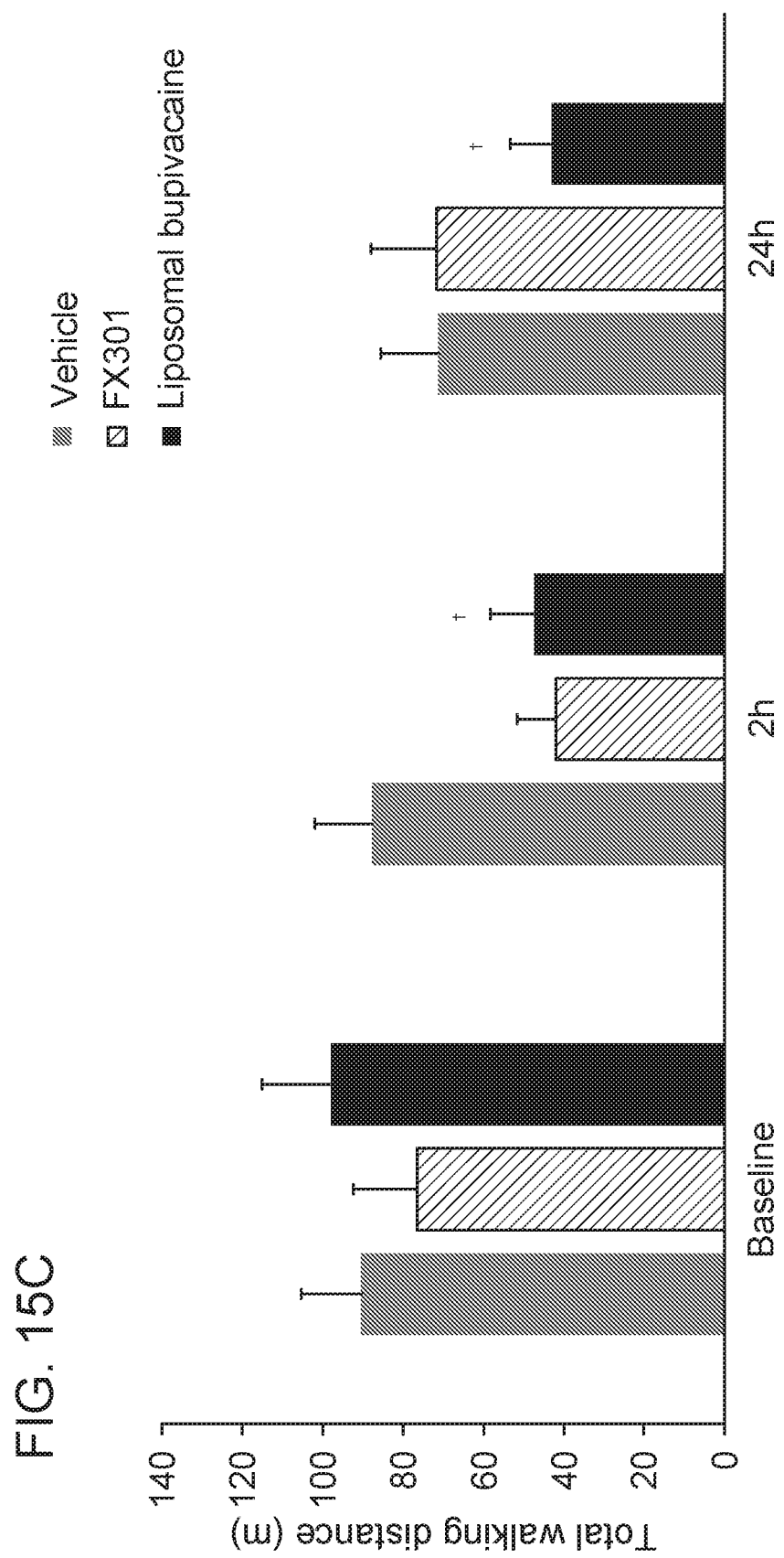

The results described herein from the von Frey testing showed an increase in withdrawal force following treatment with FX301 with a relatively long duration of activity. Compared with vehicle, withdrawal force was significantly higher in animals treated with FX301 or liposomal bupivacaine through 8 hours after injection (FIG. 15A). The results described herein show significant differences between FX301 and vehicle-treated animals persisted through 36 hours after injection; at 36 hours, the mean f SEM withdrawal force of FX301-treated animals was significantly higher than that of animals treated with vehicle or liposomal bupivacaine (vehicle: 0.76±0.08 g; FX301: 7.33±1.33 g; liposomal bupivacaine: 2.73±1.16 g; $p<0.001$ for FX301 vs vehicle and $p<0.01$ for FX301 vs liposomal bupivacaine). The results described herein show that GBS scores were highest in vehicle-treated animals, indicating greater pain and distress-related behavior in this group. The results described herein show that treatment with FX301 or liposomal bupivacaine resulted in significant reductions in GBS scores compared with vehicle through the first 12 hours after injection (FIG. 15B). The results described herein from open field testing for locomotor activity at 2 hours and 24 hours after injection showed that treatment with vehicle did not result in any alterations in the locomotor activity as assessed by total walking distance over 5 min (FIG. 15C). The results described herein show that treatment with FX301 did not significantly affect total walking distance; although a reduction in total walking distance was observed at 2 hours after injection, this was not statistically significant compared with baseline or vehicle. At 24 hours after injection, no reduction in total walking distance was evident in FX301-treated animals. In contrast, animals treated with liposomal bupivacaine experienced a significant reduction in total walking distance compared with baseline at 2 hours and 24 hours after injection.

Figure 16:
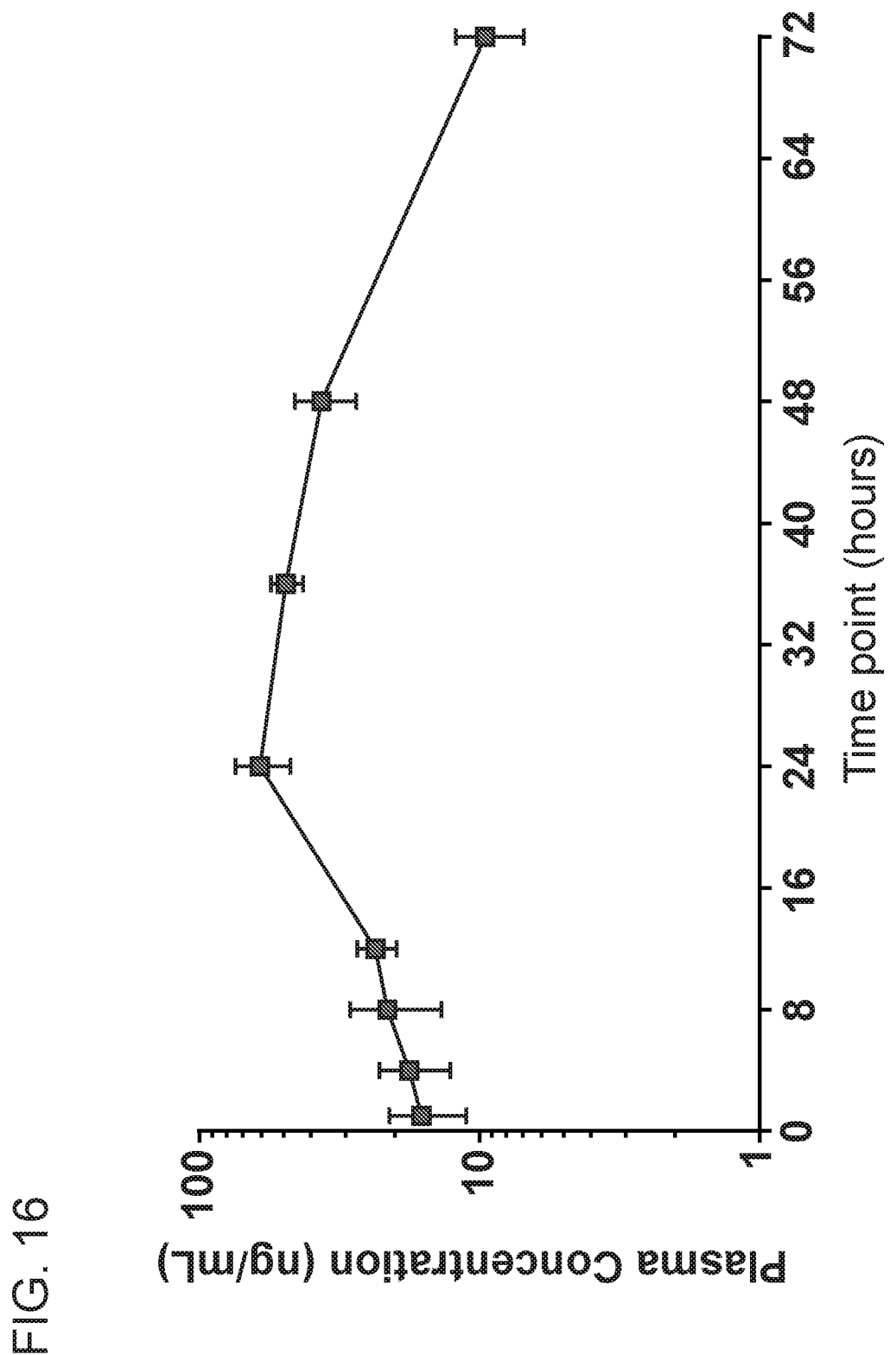
FIG. 16. Plasma funapide concentration versus time profile.

The results described herein show that mean plasma $C_{max}$ was 68.58 ng/mL and the corresponding mean $T_{max}$ was 28.00 hours (Table 10). The mean $AUC_{last}$ (mean AUC from time zero to the last quantifiable concentration) and $AUC_{inf}$ (AUC from time zero to infinity), were 2462 h·ng/mL and 2634 h·ng/mL, respectively. High plasma concentrations were maintained throughout 72 hours after injection (FIG. 16). At 72 hours after injection, measured concentrations of FX301 in muscle in each animal were 606,629.60 ng/g, 1176.99 ng/g, and 5001.73 ng/g. At 72 hours after injection, the mean measured concentration of funapide in muscle was 204,269.4 ng/g.

TABLE 10

Summary of Funapide Plasma PK Parameters
[Table 7 of provisional]

| PK parameter | FX301(n = 3) | |
|---|---|---|
| | Mean | SD |
| $t_{1/2}$ (h) | 11.62 | N/A |
| $T_{max}$(h) | 28.00 | 6.93 |
| $C_{max}$(ng/ml) | 68.58 | 10.72 |
| $AUC_{last}$ (h · ng/ml) | 2462 | 571 |
| $AUC_{inf}$ (h · ng/ml) | 2634 | 636 |

$AUC_{inf}$, area under the concentration time curve from time zero to infinity; $AUC_{last}$, area under the concentration time curve from time zero to the last quantifiable concentration; $C_{max}$, maximal plasma concentration; NA, not applicable; SD, standard deviation; $t_{1/2}$, terminal half-life; $T_{max}$, time to maximal plasma concentration.

The results described herein show that FX301 increased the withdrawal threshold following surgical incision through 36 hours after injection and improved behavior scores, consistent with less pain-related behaviors, through 12 hours after injection. No impairment of motor activity was observed with FX301, with no significant change in total walking distance at 2 and 24 hours after injection. After single administration of FX301, high local funapide concentrations were present at 72 hours. The plasma profile of funapide remained consistent with a controlled and sustained release of drug throughout the study. These results support development and use of FX301 for postoperative pain.

Example 4: Systemic and Local Funapide Concentration in Animals Treated with FX301

An in vitro drug release profile indicates consistent and extended release kinetics of funapide from the hydrogel formulation (FIG. 1A). The results described herein show that after a single, perineural injection in pigs, systemic PK profile confirms extended release from novel formulation (FIG. 17A). High local concentrations are maintained at the site of injection around the nerve, consistent with the analgesic profile (FIG. 17B). These data show that FX301 delivers funapide, a preferential Nav1.7 antagonist, locally for up to 7 days.

The results described herein, show that the composition of funapide in a tri-block PLGA-PEG-PLGA polymer as disclosed herein provides consistent and extended release of funapide that results in a high local concentration of funapide for prolonged time periods. The results described herein, show that treatment with the composition of funapide in a tri-block PLGA-PEG-PLGA polymer as disclosed herein leads to significant improvement in withdrawal force, reductions in GBS scores indicating reduction in pain and stressful behavior, and preserved motor function. These results disclosed herein support the use of the composition of the instant disclosure, in methods of treatment for, and management of post-surgical pain in a subject in need thereof.

Example 5: FX301 Drug Product (DP) Manufacturing Process

Described herein is a process for manufacturing the composition of funapide formulated in a tri-block polymer of PLGA-PEG-PLGA, of the instant disclosure. FX301 DP is a sterile injectable solution comprised of 0.5% to 1.5% (w/v) funapide formulated in 19-25% (w/w) PLGA-PEG-PLGA (1500-1500-1500 Da, LA:GA 50:50), 1-2% (w/w) DMA, 10-11% (w/w) PEG 400, and water. The DMA and PEG 400 are used as drug solubilizers that dissolve the DS, funapide, from its crystalline form. The PLGA-PEG-PLGA is a functional excipient that confers extended release and physical duration at the site of injection vis-a-vis micellar encapsulation of the drug substance and formation of a thermo-sensitive hydrogel. A flow chart depicting the formulation process is provided in FIG. 18. This allows for injection of a low-viscosity solution, similar to that of current peripheral nerve block administration procedures which then quickly transitions into a gel depot upon injection into the body.

What is claimed is:

1. A composition of funapide formulated in a PLGA-PEG-PLGA tri-block copolymer, wherein the composition comprises:

a) funapide at a concentration of 0.2 to 2% w/w;
b) a PLGA-PEG-PLGA tri-block copolymer at a concentration of 5% to 35% w/w:
   (i) wherein each Poly-Lactic-co-Glycolic acid (PLGA) polymer block has a molecular weight (MW) of 400 to 2550 Da and wherein the Polyethylene Glycol (PEG) polymer block has a MW of 1000-3000 Da; and
   (ii) wherein the PLGA comprises 40% to 100% of lactic acid (LA) and 60% to 0% of glycolic acid (GA);
c) a polar organic solvent at a concentration of 1% to 20% w/w; and
d) a solubility enhancer at a concentration of 1% to 20% w/w.

2. The composition of claim 1, wherein each PLGA polymer block has a MW of 1000-2450 Da.

3. The composition of claim 1, wherein each PLGA polymer block has a MW of 1400-2450 Da.

4. The composition of claim 1, wherein the PEG polymer block has a MW of 1000-1600 Da.

5. The composition of claim 1, wherein the funapide concentration is 0.2% to 1.8% w/w.

6. The composition of claim 1, wherein the polar organic solvent concentration is 1.5% to 20% w/w.

7. The composition of claim 1, wherein the polar organic solvent concentration is 1% to 10.5% w/w.

8. The composition of claim 1, wherein the polar organic solvent is Dimethyl acetamide (DMA), Dimethyl sulfoxide (DMSO), Glycofurol, N-Methyl-2-Pyrrolidone (NMP), or any combination thereof.

9. The composition of claim 1, wherein the solubility enhancer concentration is 5% to 20% w/w.

10. The composition of claim 1, wherein the solubility enhancer concentration is 10% to 11% w/w.

11. The composition of claim 1, wherein the solubility enhancer is Propylene Glycol (PG), Cremophor EL, Cremophor RH 60, Ethanol, Glycerin, PEG 300, PEG 400, polysorbates, Vitamin E-TPGS, PLGA-PEG diblock copolymers, hydroxypropyl-β-cyclodextrin, sulfobutyl ether-β-cyclodextrin, poloxamer 188, poloxomer 407, polyvinyl pyrrolidone (PVP), glycerol formal, Solutol HS, or any combination thereof.

12. The composition of claim 1, wherein the PLGA comprises any one of:
   a) 40% of lactic acid (LA) and 60% of glycolic acid (GA) (LA:GA ratio of 40:60);
   b) 50% of lactic acid (LA) and 50% of glycolic acid (GA) (LA:GA ratio of 50:50); and
   c) 100% of lactic acid (LA) and 0% of glycolic acid (GA) (LA:GA ratio of 100:0.

13. The composition of claim 1, wherein the PLGA-PEG-PLGA tri-block copolymer concentration is 8% to 25% w/w.

14. The composition of claim 1, wherein the total molecular weight of the total tri-block polymer system is 2500-7000 Da.

15. The composition of claim 1, wherein the total molecular weight of the total tri-block polymer system is 4000-7000 Da.

16. The composition of claim 1, wherein the PLGA-PEG-PLGA tri-block copolymer is any one of:
   a) 1000 Da-1000 Da-1000 Da of PLGA-PEG-PLGA;
   b) 1500 Da-1500 Da-1500 Da of PLGA-PEG-PLGA; and
   c) 2450 Da-1500 Da-2450 Da of PLGA-PEG-PLGA.

17. The composition of claim 1, wherein the formulation comprises:
   a) funapide at a concentration of 1.3% w/w;
   b) a PLGA-PEG-PLGA tri-block copolymer at a concentration of 19% to 19.5% w/w:
      (i) wherein each PLGA polymer block has a MW of 1500-2250 Da, and wherein the PEG polymer block has a MW of 1500 Da; and
      (ii) wherein the PLGA comprises 50% of lactic acid (LA) and 50% of glycolic acid (GA) (LA:GA ratio of 50:50);
   c) DMA at a concentration of 1.7% w/w; and
   d) PEG 400 at a concentration of 10.5% w/w.

18. The composition of claim 1, wherein the formulation comprises:
   a) funapide at a concentration of 0.65% w/w;
   b) a PLGA-PEG-PLGA tri-block copolymer at a concentration of 19% to 19.5% w/w:
      (i) wherein each PLGA polymer block has a MW of 1500-2250 Da, and wherein the PEG polymer block has a MW of 1500 Da; and
      (ii) wherein the PLGA comprises 50% of lactic acid (LA) and 50% of glycolic acid (GA) (LA:GA ratio of 50:50);
   c) DMA at a concentration of 1.7% w/w; and
   d) PEG 400 at a concentration of 10.5% w/w.

19. The composition of claim 1, wherein the composition has a dose volume of 5 ml to 40 ml.

20. A method of prevention or treatment for post-surgical pain in a subject in need thereof, wherein the method comprises administering an effective amount of the composition of claim 1.

21. A method of prevention or treatment for pain in a subject in need thereof, wherein the method comprises administering an effective amount of the composition of claim 1.

22. A method of manufacturing a composition of claim 1, the method comprising:
   i) combining and dissolving:
      a) an amount of the PLGA-PEG-PLGA tri-block polymer;
      b) an amount of water;
      c) an amount of the funapide;
      d) an amount of the polar organic solvent; and
      e) an amount of the solubility enhancer;
   to form a mixture;
   ii) stirring the mixture of (i) at 1-30° C.;
   iii) filtering the clear solution of (ii) through a sterile filter; and
   iv) collecting and freezing the filtered solution of (iii) at ≤−20° C.

23. The method of claim 22, wherein step i) comprises:
   1) compounding and dissolving the amount of the PLGA-PEG-PLGA tri-block polymer of (a) in the amount of water of (b) at 1-30° C., to form a polymer solution;
   2) dissolving the amount of the funapide of (c) in the amount of the polar organic solvent of (d) and the amount of the solubility enhancer of (e), in a separate vessel to form a funapide solution; and
   3) combining the dissolved funapide solution of (1) with the polymer solution of (2) to form a mixture.

24. The method of claim 23, wherein the combining of (3) is done at a temperature of 8-12° C.

* * * * *